United States Patent
Poss

Patent Number: 5,374,615
Date of Patent: Dec. 20, 1994

[54] INDOLE- AND BENZIMIDAZOLE-SUBSTITUTED IMIDAZOLE AND BENZIMIDAZOLE DERIVATIVES

[75] Inventor: Michael A. Poss, Lawrenceville, N.J.

[73] Assignee: E. R. Squibb & Sons, Inc., Princeton, N.J.

[21] Appl. No.: 838,492

[22] Filed: Feb. 7, 1992

Related U.S. Application Data

[63] Continuation-in-part of Ser. No. 739,126, Jul. 31, 1991, abandoned, which is a continuation-in-part of Ser. No. 606,631, Oct. 31, 1990, abandoned.

[51] Int. Cl.⁵ ............... A61K 31/415; A61K 31/435; C07D 487/04; C07D 417/12; C07D 403/06; C67D 263/54

[52] U.S. Cl. .................. 514/3.81; 514/234.5; 514/394; 514/395; 514/397; 548/252; 548/253; 548/254; 548/306.1; 548/312.1

[58] Field of Search ............... 548/327, 328, 252, 253, 548/254, 306.1, 312.1; 514/394, 395, 381, 234.5, 397

[56] References Cited

U.S. PATENT DOCUMENTS

| | | | |
|---|---|---|---|
| 4,207,324 | 6/1980 | Matsumura et al. | 548/336 |
| 4,340,598 | 7/1982 | Furukawa et al. | 548/337 |
| 4,355,040 | 10/1982 | Furukawa et al. | 548/336 |
| 4,582,847 | 4/1985 | Furukawa et al. | 514/400 |
| 4,812,462 | 3/1989 | Blankley et al. | 514/303 |
| 4,816,463 | 3/1989 | Blankley et al. | 514/293 |
| 4,820,843 | 4/1989 | Aldrich et al. | 548/252 |
| 4,859,684 | 8/1989 | Raeymaekers et al. | 548/327 |
| 4,870,186 | 9/1989 | Aldrich et al. | 548/215 |
| 4,874,867 | 10/1989 | Aldrich et al. | 548/101 |
| 4,880,804 | 11/1989 | Carini et al. | 514/234.5 |
| 5,177,074 | 1/1993 | Allen et al. | 514/234.5 |
| 5,212,195 | 5/1993 | Clark et al. | 548/254 |

FOREIGN PATENT DOCUMENTS

| | | |
|---|---|---|
| 328203 | 6/1989 | European Pat. Off. |
| 356234 | 8/1989 | European Pat. Off. |
| 450566 | 4/1991 | European Pat. Off. |

*Primary Examiner*—Floyd D. Higel
*Attorney, Agent, or Firm*—Theodore R. Furman, Jr.; Ellen K. Park

[57] ABSTRACT

Novel compounds are disclosed having the formula

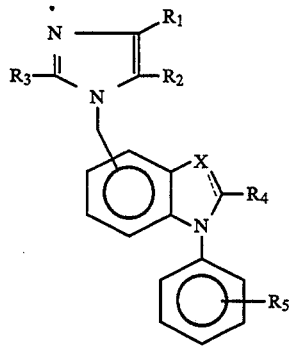

wherein X, $R_1$, $R_2$, $R_3$, $R_4$, and $R_5$ are substituents. These compounds inhibit the action of angiotensin II and are useful, therefore, for example, as antihypertensive agents.

20 Claims, No Drawings

INDOLE- AND BENZIMIDAZOLE-SUBSTITUTED IMIDAZOLE AND BENZIMIDAZOLE DERIVATIVES

This is a continuation-in-part of U.S. Ser. No. 739,126 filed Jul. 31, 1991, abandoned which is a continuation-in-part of U.S. Ser. No. 606,631 filed Oct. 31, 1990 abandoned.

FIELD OF THE INVENTION

The present invention relates to novel substituted imidazoles which are useful as antihypertensive agents.

SUMMARY OF THE INVENTION

In accordance with the present invention, novel compounds which inhibit the action of the hormone angiotensin II are disclosed. These compounds are of the general formula

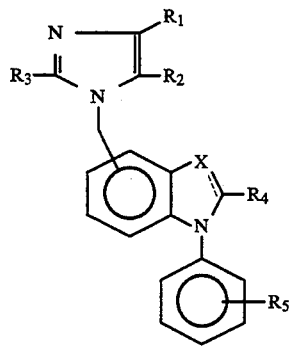

I including pharmaceutically acceptable salts and prodrugs thereof;

where X can be —N— or

when X=N, the double bond is always present;
$R_1$ is hydrogen, halogen, —$NO_2$, haloalkyl or —CN;
$R_2$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; —$(CH_2)_m$-imidazol-1-yl; —$(CH_2)_m$-1,2,3-triazolyl optionally substituted with one or two groups selected from $CO_2R_7$ or alkyl of 1 to 4 carbon atoms; —$(CH_2)_m$-tetrazolyl; —$(CH_2)_n OR_6$;

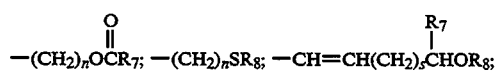

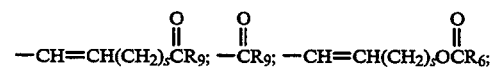

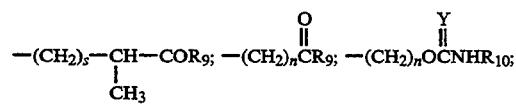

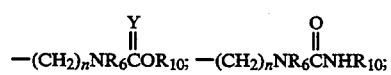

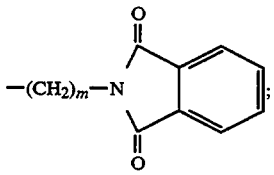

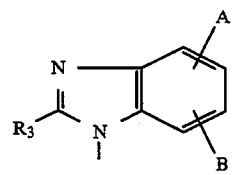

or $R_1$ and $R_2$ taken together with the carbon atoms of the imidazole nucleus to which they are attached can form a benzimidazole shown as

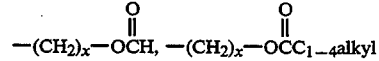

wherein A can be hydrogen, alkyl, $C_xF_{2x+1}$, $C_6F_5$, halogen, $C_{1-6}$alkoxy, —$(CH_2)_xOH$, —$(CH_2)_x$—$OC_{1-4}$alkyl, —$(CH_2)_x$—OCH, —$(CH_2)_x$—$OCC_{1-4}$alkyl
         ||              ||
         O               O or —$COR_9$ and B can be hydrogen, alkyl, $C_xF_{2x+1}$, $C_6F_5$, halogen or $C_{1-6}$alkoxy;

$R_3$ is alkyl of 2 to 10 carbon atoms, alkenyl or alkynyl of 3 to 10 carbon atoms or the same groups substituted with F or $CO_2R_7$; cycloalkyl of 3 to 8 carbon atoms, cycloalkylalkyl of 4 to 10 carbon atoms; cycloalkylalkenyl or cycloalkylalkynyl of 5 to 10 carbon atoms; $(CH_2)_sZ(CH_2)_mR'$ (wherein R' is H, $C_{1-6}$alkyl, $C_{3-6}$cycloalkyl, $C_{2-4}$alkenyl or $C_{2-4}$alkynyl) optionally substituted with F or $CO_2R_7$; benzyl or benzyl substituted on the phenyl ring with 1 or 2 halogens, alkoxy of 1 to 4 carbon atoms, alkyl of 1 to 4 carbon atoms or nitro;

$R_4$ and $R_4'$ are independently selected from hydrogen, halogen, haloalkyl, alkyl, aryl, cycloalkyl, aralkyl,

$R_5$ is hydrogen,

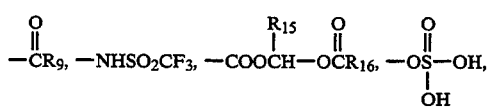

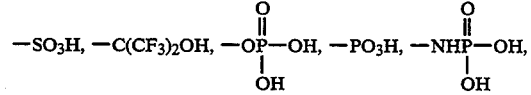

-continued

—NHSO₂CF₃, —CONHOR₁₅, $-\underset{R_{19}}{\underset{|}{C}}-\underset{OH}{\overset{O}{\overset{\|}{P}}}-OH,$

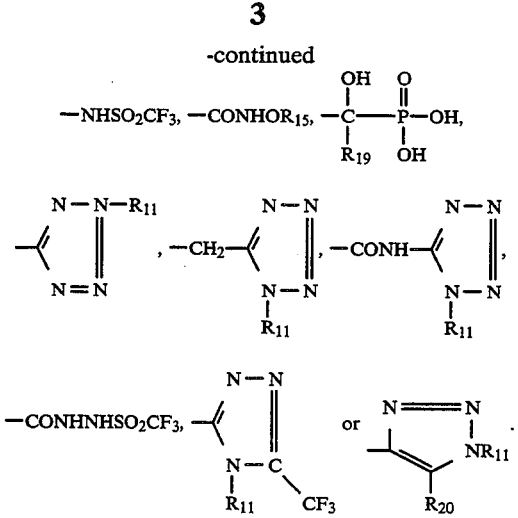

$R_6$ is H, alkyl of 1 to 6 carbon atoms, cycloalkyl of 3 to 6 carbon atoms, phenyl or benzyl;

$R_7$ is H, alkyl or perfluoroalkyl of 1 to 8 carbon atoms, cycloalkyl of 3 to 6 carbon atoms, phenyl or benzyl;

$R_8$ is H, alkyl of 1 to 6 carbon atoms, cycloalkyl of 3 to 6 carbon atoms, phenyl, benzyl, acyl of 1 to 4 carbon atoms, phenacyl;

$R_9$ is H, alkyl of 1 to 6 carbon atoms, cycloalkyl of 3 to 6 carbon atoms, $(CH_2)_pC_6H_5$, $OR_{11}$ or $NR_{12}R_{13}$;

$R_{10}$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R_{11}$ is H, alkyl of 1 to 6 carbon atoms, cycloalkyl of 3 to 6 carbon atoms, aryl, arylalkyl, a 5- to 7-membered carbocyclic ring which may have another 5- to 7-membered carbocyclic ring fused thereto,

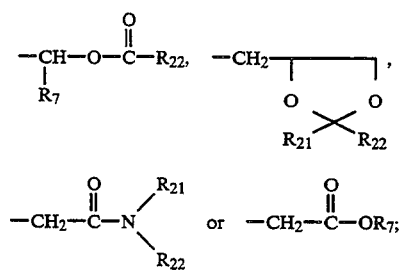

or a metal ion, M, such as Na or Li $R_{12}$ and $R_{13}$ independently are H, alkyl of 1 to 4 carbon atoms, phenyl, benzyl, α-methylbenzyl, or taken together form a ring of the formula

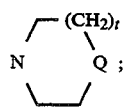

Q is $NR_{14}$, O or $CH_2$;

$R_{14}$ and $R_{15}$ are independently H, alkyl, aryl, aralkyl or cycloalkyl;

$R_{16}$ is $C_{1-6}$alkyl —$NR_{17}R_{18}$ or

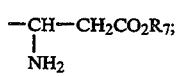

$R_{17}$ and $R_{18}$ are independently H, $C_{1-6}$alkyl, benzyl or taken together are 3 to 6 carbon atoms forming a 4- to 7-membered ring with the nitrogen atom to which they are attached;

$R_{19}$ is H, $C_{1-5}$alkyl, phenyl;

$R_{20}$ is —CN, —NO₂ or —CO₂R₇;

wherein $R_{21}$ is hydrogen, alkyl, cycloalkyl, aryl or arylalkyl and $R_{22}$ is hydrogen, alkyl, cycloalkyl, aryl, arylalkyl or alkoxy or together $R_{21}$ and $R_{22}$ are —(CH₂)₂—, —(CH₂)₃—, —CH=CH— or

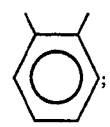

Y=O or S;
Z=O, NR₆ or S;
m is 1-5;
n is 1-10;
p is 0-3;
q is 2-3;
r is 0-2;
x is 1 to 6.

DETAILED DESCRIPTION OF THE INVENTION

The present invention relates to the compounds of formula I and to pharmaceutical compositions and methods employing such compounds.

The term "aryl", as used throughout the specification either by itself or as part of a larger group, refers to phenyl or phenyl substituted with halogen, alkyl, alkoxy, alkylthio, hydroxy, alkanoyl, nitro, amino, dialkylamino, or trifluoromethyl groups. Phenyl and monosubstituted phenyl are preferred and phenyl is the most preferred.

The term "alkyl", as used throughout the specification either by itself or as part of a larger group, refers to groups having 1 to 10 carbon atoms. Alkyl groups having 1 to 4 carbon atoms are preferred.

The term "cycloalkyl", as used throughout the specification either by itself or as part of a larger group, refers to groups having 3 to 7 carbon atoms.

The term "alkoxy", as used throughout the specification either by itself or as part of a larger group, refers to groups having 1 to 8 carbon atoms. Alkoxy groups having 1 to 3 carbon atoms are preferred.

The term "halogen", as used by itself or as part of a larger group refers to fluorine, chlorine, bromine and iodine with fluorine and chlorine being preferred.

It should be understood that the present invention is meant to include prodrug forms, i.e. ester, acetal and/or mixed acetal derivatives, of compounds of formula I. For example, such derivatives have been documented in *Design of Prodrugs*, edited by H. Bundgard, (Elsevier, 1985) and *Methods in Enzymology*, Vol. 42, p. 309-396, edited by K. Widder et al. (Academic Press, 1985). While prodrug forms of compounds of formula I are generally represented by the compounds herein wherein one or more $R_{11}$ groups (where $R_{11}{\neq}H$) are present at $R_2$, $R_4$ and/or $R_5$, it is understood that any moiety at $R_{11}$ which will be cleaved in vivo to provide the compounds of formula I where $R_{11}$=hydrogen is within the scope and spirit of this invention.

To prepare the compounds of formula I where $R_4'=H$, $R_4=H$, and the double bond is present, X is
—C— and where $R_1$ and $R_2$ do not form a benzene
ring, a compound of the formula

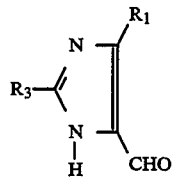  II (when $R_1$ is other than haloalkyl)
or

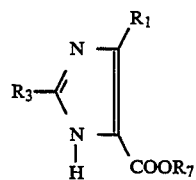  II'

(when $R_1$ is haloalkyl) is coupled with a compound
of the formula

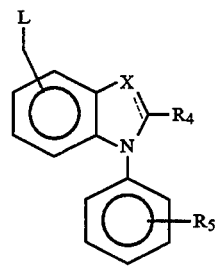  III wherein L is a leaving group such as a halogen, in the presence of a coupling agent, e.g., potassium hexamethyldisilazane, in solvents such as tetrahydrofuran and dimethylformamide, to provide the compound

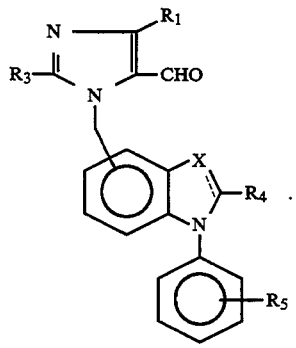  IV

Aldehyde IV can thereafter be treated with a reducing agent, such as sodium borohydride, in a solvent such as ethanol to provide

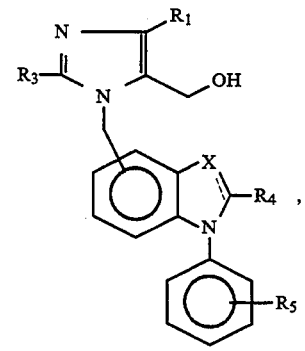  Ia that is, compounds of formula I wherein $R_2$ is —CH$_2$—OH. Using known techniques, compounds of formula I where $R_2$ is other than —CH$_2$OH can be prepared from compound Ia. For example, alcohols of formula Ia can be alkylated or acylated to provide the corresponding products of formula I. Alternatively, compounds of formula I can be prepared from IV by Wittig homologation of the aldehyde.

The imidazole aldehyde II (i.e., where $R_1$ is other than haloalkyl) can be prepared by treating a compound of the formula

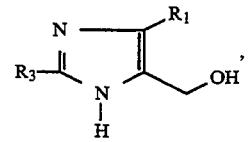  V in pyridine, with an oxidizing agent, e.g., manganese oxide.

Compounds of formula III can be prepared by coupling a compound of the formula

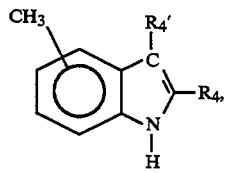  VI with a compound of the formula

  VII where X is halo, e.g., bromine, for example, in pyridine and in the presence of copper oxide, to provide compounds of the formula

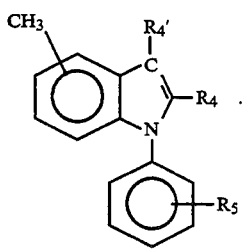  VIII

A leaving group, L, for example a halogen such as bromide, can be added by known methodology to provide compounds of the formula

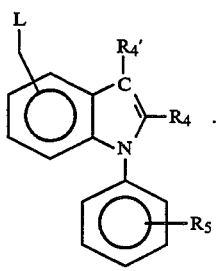  IIIa

Compounds of formula VI can be prepared by known techniques such as those described in *J. Heterocyclic Chem.*, 25, 1 (1988).

Compounds of formula I where X is nitrogen can be prepared by reacting a compound of the formula

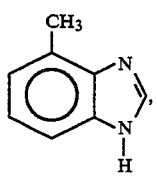  IX prepared as described by Mathias et al., *Synthetic Communications*, 5, 461–469 (1975), with a compound of the formula

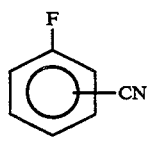  X in the presence of a base, e.g., potassium carbonate, and in a solvent, e.g., dimethylformamide, to provide a compound of the formula

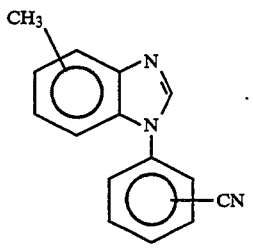  XI

Compound XI can thereafter be treated with N-bromosuccinimide and a radical initiator, e.g., 2,2'-azobisisobutyronitrile, in a solvent, e.g., carbon tetrachloride, to provide a compound of the formula

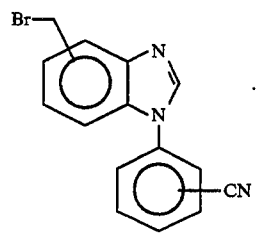  XII

Intermediate XII can be coupled with the aldehyde of formula II to provide

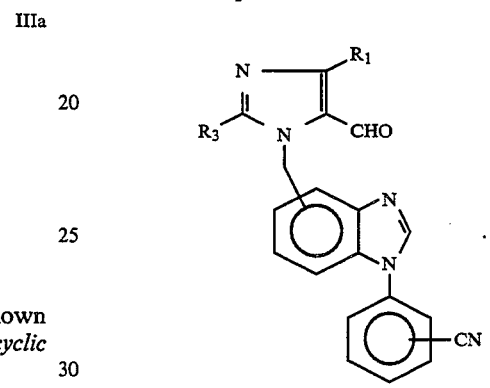  XIII

The aldehyde XIII can be treated as the aldehyde IV above to provide

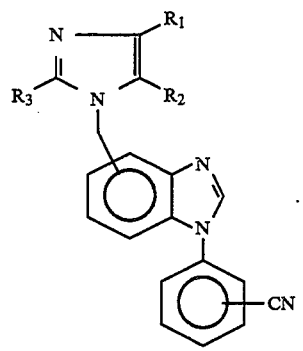  XIV

Compound XIV can then be reacted with a compound of the formula (n-Bu)$_3$SnN$_3$ to provide compounds of formula I where X is nitrogen and R$_5$ is

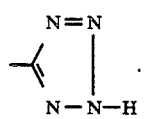

Compounds of formula I where X is nitrogen and R$_5$ is other than

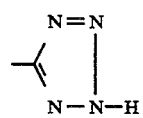

can be prepared by using intermediate VII in place of compound X above.

The compounds of formula I wherein $R_1$ and $R_2$ together with the imidazole nucleus to which they are attached form a benzimidazole can be prepared using the methodology in U.S. Pat. No. 4,880,804.

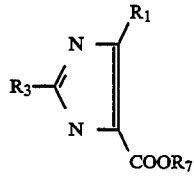  II'

(i.e., where $R_1$ is haloalkyl ) can be prepared by, first treating a compound of the formula

  XV with for example, sodium nitrite, and an acid, e.g., acetic acid, to provide the intermediate

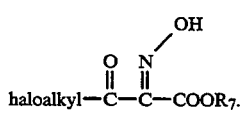  XVI

This can thereafter be treated with an aldehyde such as $R_3CHO$   XVII and in the presence of ammonium hydroxide, to provide

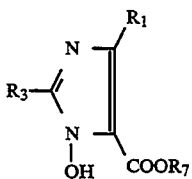  XVIII which is thereafter reduced, e.g., with $TiCl_3$ in the presence of a buffer, e.g., sodium acetate, to provide the compound of formula II'.

Compounds of formula I where X is nitrogen can be prepared by coupling a compound of the formula

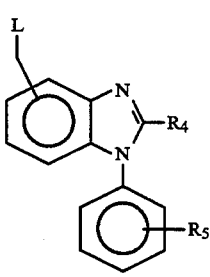  IIIb with a compound of formula II or II' as described above for the coupling of compounds II and III.

Compounds of formula IIIb can be prepared using known methodology. For example, to prepare a compound of formula IIIb wherein $R_4$ is haloalkyl, first a compound of the formula

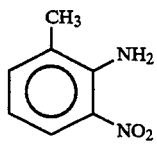  XIX is reacted with a compound of the formula

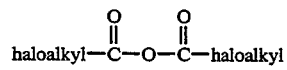  XX in solvents, e.g., dioxane and pyridine, to provide the intermediate

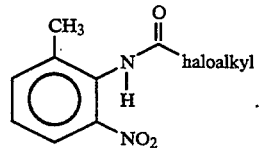  XXI

Compound XXI can be treated with a reducing agent, such as zinc in the presence of an acid, such as sulfuric acid in solvents, e.g., water and methanol, to provide

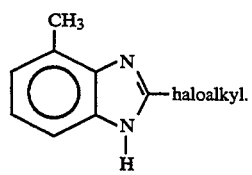  XXII

Compound XXII can thereafter be treated as compounds IX, XI, XII, XIII and XIV above to provide the corresponding products of formula I.

Compounds of formula IIIb where $R_4$ is halogen, e.g., F or Br, can be prepared by treating a compound of formula IX above with a nitrogen protecting group, e.g., $(CH_3)_3SiCH_2CH_2-OCH_2Cl$, in the presence of a base such as sodium hydride and in a solvent, e.g., tetrahydrofuran, to provide, for example,

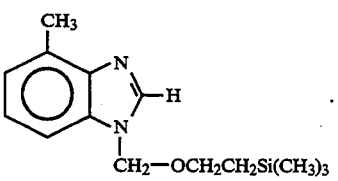  XXIII

Compound XXIII is then treated with a base, such as n-butyl lithium followed by treatment with either

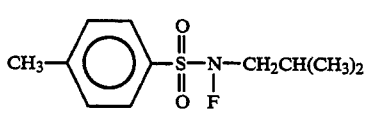  XXIV (prepared as described by W. E. Barnette, *J. Amer. Chem. Soc.*, Vol. 106, p. 452–454 (1984)) for intermediates where $R_4=F$, or N-bromosuccinimide where $R_4=Br$ to provide the corresponding intermediates

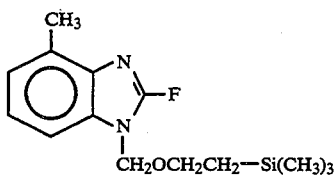

XXVa and

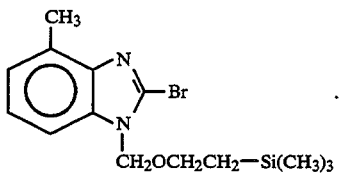

XXVb

Using known technology, e.g., treatment with n-tetrabutyl ammonium fluoride in tetrahydrofuran, compounds of formulae XXVa and XXVb can be converted to

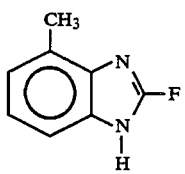

XXVIa and

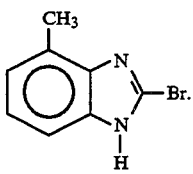

XXVIb

The so-prepared intermediates can thereafter be subjected to the methodology above to provide the corresponding products of formula I.

Prepared compounds of formula I can be shown generally as

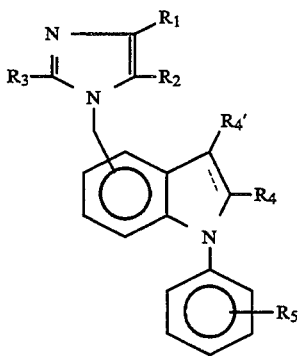

I' or

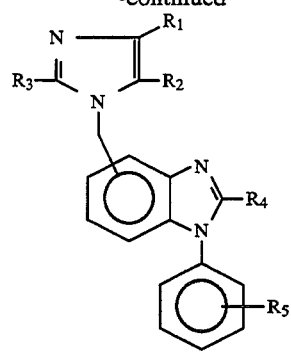

I'' where $R_1$-$R_5$ are as defined above for formula I.

Most preferred are those compounds of formula I' where $R_1$ is hydrogen, halogen or haloalkyl;
$R_2$ is —CH$_2$OH, —CHO or —COOR$_{11}$;
$R_3$ is C$_{2-10}$alkyl or C$_{3-10}$alkenyl;
$R_4$ and $R_4'$ are H or —COOH; and,
$R_5$ is ortho-tetrazole which may be substituted with $R_{11}$ or —COOR$_{11}$; or the compounds of formula I'' wherein
$R_1$ is hydrogen, halogen or haloalkyl;
$R_2$ is —CH$_2$OH, —CHO or —COOR$_{11}$;
$R_3$ is C$_{2-10}$alkyl or C$_{3-10}$alkenyl;
$R_4$ is H, halogen (preferably Br or F) or haloalkyl (preferably CF$_3$); and
$R_5$ is ortho-tetrazole which may be substituted with $R_{11}$ or —COOR$_{11}$.

The present compounds of formula I inhibit the action of the hormone angiotensin II (A-II) and are therefore useful, for example, as antihypertensive agents.

The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention inhibit the action of A-II at its receptors on target cells and thus prevent the increase in blood pressure produced by this hormonereceptor interaction. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg per kilogram of body weight per day, preferably about 1 to 15 mg per kilogram of body weight per day is appropriate to reduce blood pressure. The substance is preferably administered orally, but intranasal, transdermal and parenteral routes such as the subcutaneous, intramuscular, intravenous or intraperitoneal routes can also be employed. The compounds of this invention are also useful in the treatment of congestive heart failure and cardiac hypertrophy, based on their action on the active pressor substance, angiotensin II, they are also expected to be useful in situations where ACE inhibitors are useful.

The compounds of this invention can also be formulated in combination with a diuretic for the treatment of hypertension. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian species in need thereof. Exemplary of the diuretics contemplated for use in combination with a peptide of this invention are the thiazide diuretics, e.g., chlorthiazide, hydrochlorthiazide, flumethiazide, hydroflumethiazide, bendroflumethiazide, methylchlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The present invention can be further illustrated by the following examples.

EXAMPLE 1

5-[[2-Butyl-5-(hydroxymethyl)-1H-imidazol-1-yl]-methyl]-1-(2-carboxyphenyl)-1H-indol-2-carboxylic acid, dilithium salt

A.

2-[(4-Methylphenyl)hydrazono]propanoic acid, ethyl ester para-Tolylhydrazine (1.2024 g, 9.84 mmol, 1.0 eq.) was combined with ethyl pyruvate (1.08 ml, 9.84 mmol, 1.0 eq.) and 3A sieves (3.6 g, 300% by weight) in methylene chloride (9.8 ml, 1M) at room temperature. After 30 minutes, the reaction was filtered through anhydrous magnesium sulfate and concentrated to give the title A compound (2.095 g) which was used in the next step without purification or characterization.

B.

5-Methyl-1H-indole-2-carboxylic acid, ethyl ester

The title A compound (2.095 g, 9.51 mmol, 1.0 eq) was dissolved in absolute ethanol (9.8 ml, 1M) and hydrochloric acid gas was bubbled through the reaction until it showed no starting material (45 minutes). The reaction solution was then concentrated, dissolved in ethyl acetate, and washed once with aqueous saturated sodium hydrogen carbonate. The organic phase was then dried over sodium sulfate, filtered through magnesium sulfate and concentrated. The residue was chromatographed on silica gel (60 g) eluting with toluene followed by chloroform:hexane (1:4) followed by ether:hexane (2:3) to give the title B compound (1.5187 g).

C.

2-Bromobenzoic acid, ethyl ester

2-Bromobenzoic acid (2.005 g, 9.47 mmol, 1.0 eq.) was combined with iodoethane (1.60 ml, 19.9 mmol, 2.0 eq.) and sodium bicarbonate (1.68 g, 19.9 mmol, 2.0 eq.) in dimethylformamide (10 ml, 1M) and stirred at room temperature for a total of 4 days. The reaction was then diluted with water (20 ml) and extracted with ether:hexane (1:1, 3×20 ml). The combined organic extracts were washed with aqueous 10% sodium hydrogen sulfite (20 ml), water (20 ml), and aqueous saturated sodium chloride (20 ml). Next, the organic extracts were dried over sodium sulfate, filtered through magnesium sulfate and concentrated. The residue was chromatographed on silica gel (50 g) eluting with ether:hexane (1:6) to furnish the title C compound (2.17 g).

D.

1-[2-(Ethoxycarbonyl)phenyl]-5-methyl-1H-indole-2-carboxylic acid, ethyl ester

The title B compound (603 mg, 2.97 mmol, 1.0 eq.) was combined with the title C compound (1.699 g, 7.42 mmol, 2.5 eq.) and copper(I)oxide (424 mg, 2.97 mmol, 1.0 eq.) in pyridine (3.0 ml, 1M) and heated at 130° C. for 3 hours. The reaction was then cooled, diluted with ethyl acetate, combined with an earlier run of this title D compound and filtered through celite. The filtrate was washed with water (3×30 ml), 0.5N hydrochloric acid (2×30 ml) and aqueous saturated sodium hydrogen carbonate (1×30 ml). The organic solution was then dried over sodium sulfate, filtered through magnesium sulfate and concentrated. The residue was chromatographed on silica gel (45 g) eluting with ether:hexane (1:8) to provide the title D compound (1.0246 g).

E.

5-(Bromomethyl)-1-[2-(ethoxycarbonyl)-phenyl]-1H-indole-2-carboxylic acid, ethyl ester The title D compound (1.0084 g, 2.87 mmol, 1.0 eq.) was combined with N-bromosuccinimide (531.4 mg, 2.96 mmol, 1.03 eq.) and azobisisobutyronitrile (20.2 mg, 2% by weight) in carbon tetrachloride (47.8 ml, 0.06M) and heated at 80° C. for 2 hours. The reaction was then cooled to 0° C., filtered and concentrated. The residue was chromatographed on silica gel (45 g) eluting with ether: hexane (1:8) followed by (1:5) to give the title E compound (1.0524 g).

F.

Pentanimidic acid ethyl ester hydrochloride

Hydrogen chloride gas was bubbled into a tared solution of valeronitrile (92.0 g, 1.08 mole) in absolute ethanol (64 ml, 1.08 mole) in a 1-liter round bottomed flask cooled to 0° C. The flask was weighed periodically and hydrogen chloride gas bubbling was continued until the weight gain was greater than 39 g (1.08 mole). The mixture was then stoppered and stored at 0° C. for 6 days. Ether (650 ml) was then added (cold) and the mixture was stored at −30° C. for 24 hours. The resulting solid was collected on a buchner funnel, transferred quickly to a large beaker, triturated quickly with cold ether, and collected again on a buchner funnel. The solid was then dried in vacuum to give the title F compound as a free flowing white solid (95 g).

G.

2-Butyl-4-(hydroxyethyl)imidazole

A 300 ml stainless steel Parr pressure bomb containing dihydroxyacetone dimer (5.0 g, 55 mmol) was cooled in a dry ice bath for one hour. During the cooling period, the bomb lid was set on top of the bomb and held in place by applying a light vacuum; the associated hardware for holding the lid in place under pressure was not cooled (to facilitate handling later). When the bomb was sufficiently cooled, liquid ammonia was condensed into a 250 ml three neck flask fitted with a dry ice condenser at −78° C. The cold bomb was then opened by releasing the vacuum, the title F compound (9.1 g, 55 mmol) was added, followed immediately by liquid ammonia from the 250 ml flask (approx. 55 ml of ammonia were added). The bomb was sealed using the appropriate hardware, removed from the dry ice bath, and allowed to warm to room temperature. The bomb was then immersed about half way in an oil bath and heated to 75° C. for three hours, during which the pressure rose to 320 psi. Heating was then discontinued and the bomb was allowed to cool to room temperature. When the pressure dropped below 100 psi, the pressure relief valve was slowly opened and the ammonia was allowed to evaporate (evaporative cooling helped cool the bomb). When the pressure was completely equilibrated, the bomb was opened and its contents were transferred to a conventional flask using acetonitrile to wash the residue out. The mixture was concentrated in vacuo and the residue was purified by flash chromatography on silica gel (1500 g), eluting with 80:20:1 chloroform:methanol:ammonium hydroxide. Fractions containing the major product ($R_f$ 0.5) were combined and concentrated. The residue was then crystallized from acetonitrile (200 ml) to give the title G compound as a white crystalline solid (5.74 g), m.p. 92–93° C.

H.

2-Butyl-1H-imidazole-5-carboxaldehyde

The title G compound (3.0 g, 19.5 mmol, 1.0 eq.) was dissolved in pyridine (100 ml, 0.2M) and heated to 100° C. Manganese(IV)oxide (20 g, 230 mmol, 11.8 eq.) was added and the reaction was stirred for 1 hour at 100° C. The reaction was then filtered and concentrated. The residue was triturated from ether to give the title H compound (2.0 g), m.p. 113.5–114.5° C.

I.

5-[(2-Butyl-5-formyl-1H-imidazol-1-yl)-methyl]-1-[2-(ethoxycarbonyl)phenyl]-1H-indole-2-carboxylic acid, ethyl ester The title H compound (207.4 mg, 1.36 mmol, 1.1 eq.) was dissolved in tetrahydrofuran (3.09 ml, 0.44M) and dimethylformamide (1.03 ml, 1.3M), cooled to 0° C. and treated with potassium hexamethyldisilazane (1.90 ml, 1.42 mmol, 1.15 eq. 0.75M in toluene). The reaction was stirred for 10 minutes at 0° C., warmed to room temperature and then the title E compound (533 mg, 1.24 mmol, 1.0 eq.) in tetrahydrofuran (2.0 ml, 0.6M) was added. The reaction was stirred for 4 hours, quenched with aqueous saturated ammonium chloride, and extracted three times with ethyl acetate. The organic extracts were dried over sodium sulfate, filtered through magnesium sulfate and concentrated. The residue was chromatographed on silica gel (20 g) eluting with toluene:acetone (8:1) to furnish the title I compound (517 mg).

J.

5-[[2-Butyl-5-(hydroxymethyl)-1H-imidazol-1-yl]methyl]-1-[2-(ethoxycarbonyl)phenyl]-1H-indole-2-carboxylic acid, ethyl ester The title I compound (517 mg, 1.03 mmol, 1.0 eq.) was dissolved in absolute ethanol (10.3 ml 0 1M) cooled to 0° C. and treated with $NaBH_4$ (38.8 mg dissolved in 3.9 ml of absolute ethanol, 1.03 mmol, 1.0 eq.). The reaction was stirred for 20 minutes at 0° C., quenched with 1N hydrochloric acid to pH=4, and concentrated. The residue was dissolved in water and extracted three times with ethyl acetate. The organic extracts were dried over sodium sulfate, filtered through magnesium sulfate and concentrated. The residue was chromatographed on silica gel (20 g) eluting with chloroform:methanol:ammonium hydroxide (30:1.2:0.05) to give the title J compound (345 mg).

K.

5-[[2-Butyl-5-(hydroxymethyl)-1H-imidazol-1-yl]methyl]-1-(2-carboxyphenyl)-1H-indol-2-carboxylic acid, dilithium salt The title J compound (345 mg, 0.685 mmol, 1.0 eq.) was dissolved in methanol (5.0 ml, 0.14M) and treated with aqueous 1N lithium hydroxide (5.0 ml, 5.0 mmol, 7.3 eq.). The reaction was stirred at room temperature for 20 hours and concentrated. The residue was dissolved in water and chromatographed on HP-20 (20 g) eluting with water (100 ml), 1% acetone in water (120 ml), 3% acetone in water (120 ml) and 5% acetone in water (120 ml). The material was concentrated to a volume of approximately 50 ml and lyophilized. After obtaining carbon and proton NMR spectra, the product was dissolved in water, filtered through a polycarbonate membrane and lyophilized to furnish the title compound (277.4 mg).

EXAMPLE 2

2-[5-[[2-Butyl-5-(hydroxymethyl)-1H-imidazol-1-yl]methyl]-1H-indol-1-yl]benzoic acid, monolithium salt

A.

2-(5-Methyl-1H-indol-1-yl)benzoic acid, ethyl ester

5-Methylindole (730.6 mg, 5.57 mmol, 1.0 eq.) was combined with the title C compound of Example 1 (3.189 g, 13.9 mmole, 2.5 eq.) and copper(I)oxide (797 mg, 5.57 mmol, 1.0 eq.) in pyridine (5.6 ml, 1M). The reaction was heated at 120° C. for 3 hours, cooled to room temperature, diluted with ethyl acetate and filtered through celite. The filtrate was washed twice with water, twice with aqueous 1N hydrochloric acid, and once with aqueous saturated sodium hydrogen carbonate. The organic phase was then dried over sodium sulfate, filtered through magnesium sulfate and concentrated. The residue was chromatographed on silica gel (50 g) eluting with hexane:ether (40:1) followed by (20:1) to give 848 mg of the title A compound.

B.

2-[3-(or 2,3-Di)bromo-5-(bromomethyl)-1H-indol-1-yl]benzoic acid, ethyl ester

The title B compound (834.7 mg, 2.99 mmol, 1.0 eq.) was combined with N-bromosuccinimide (1.074 g, 6.04 mmol, 2.02 eq.) and azobisisobutyronitrile (25.0 mg, 3% by weight) in carbon tetrachloride (49.8 ml, 0.06M) and heated at 80° C. for 2½ hours. The reaction was cooled to room temperature and concentrated. The residue was dissolved in chloroform (5 ml) and ether:hexane (1:1, 50 ml), filtered and concentrated. The product was chromatographed on silica gel (50 g) eluting with hexane:ether (30:1) followed by (15:1) to provide 747.7 mg of a mixture of di-brominated and tri-brominated title B material.

C.

2-[3-(or 2,3-Di)bromo-5-[(2-butyl-5-formyl-1H-imidazol-1-yl)methyl]-1H-indol-1-yl]-benzoic acid, ethyl ester The title H compound of Example 1 (273.7 mg, 1.80 mmol, 1.15 eq.) was dissolved in tetrahydrofuran (3.90 ml, 0.46M) and dimethylformamide (1.30 ml, 1.4M), cooled to 0° C. and treated with potassium hexamethyldisilazane (2.68 ml, 1.88 mmol, 1.2 eq., 0.7M in toluene). The reaction was warmed to room temperature for 15 minutes, cooled to 0° C. and then the title B mixture (607.1 mg, 1,56 mmol, 1.0 eq.) in tetrahydrofuran (1.56 ml, 1M) was added. The ice bath was allowed to melt and the mixture was stirred at room temperature for a total of three days. The reaction was quenched with aqueous saturated ammonium chloride (15 ml) and extracted with ethyl acetate (3×15 ml). The organic extracts were dried over sodium sulfate, filtered through magnesium sulfate and concentrated. The residue was chromatographed on silica gel (35 g) eluting with toluene:acetone (14:1) followed by (10:1) to give 469.2 mg of a mixture of monobrominated and di-brominated title C material.

D.

2-[3-(or 2,3-Di)bromo-5-[[2-butyl-5-(hydroxymethyl)-1H-imidazol-1-yl]methyl]-1H-indol-1-yl]benzoic acid, ethyl ester The title C mixture (469.2 mg, 1.02 mmol, 1.0 eq.) was dissolved in absolute ethanol (10.2 ml, 0.1M) and treated at room temperature with NaBH$_4$ (38.6 mg dissolved in 3.9 ml of absolute ethanol, 1.02 mmol, 1.0 eq.). The reaction was stirred at room temperature for 1 hour, quenched with 1N hydrogen chloride until acidic and concentrated. The residue was dissolved in water and extracted three times with ethyl acetate. The organic extracts were dried over sodium sulfate, filtered through magnesium sulfate and concentrated. The residue was chromatographed on silica gel (18 g) eluting with chloroform:methanol: ammonium hydroxide (30:0.8:0.05) followed by (30:1:0.05) followed by (30:2:0.05) to furnish 466.1 mg of a mixture of monobrominated and di-brominated title D material.

E.

2-[5-[[2-Butyl-5-(hydroxymethyl)-1H-imidazol-1-yl]methyl]-1H-indol-1-yl]-benzoic acid, ethyl ester The title D mixture (420 mg, 0.823 mmol, 1.0 eq.) was combined with triethyl amine (0.34 ml, 2.47 mmol, 3.0 eq.) and palladium hydroxide on carbon (84 mg, 20% by weight) in absolute ethanol (16.4 ml, 0.05M) and placed under a balloon of hydrogen gas at room temperature for 45 minutes. The reaction was then diluted with ethanol, filtered through regenerated cellulose and concentrated. The residue was chromatographed on silica gel (10 g) eluting with hexane:acetone: ammonium hydroxide (20:10:0.05) followed by (20:20:0.05) followed by (10:20:0.05) to give the title E compound (321.3 mg).

F.

2-[5-[[2-Butyl-5-(hydroxymethyl)-1H-imidazol-1-yl]methyl]-1H-indol-1-yl]benzoic acid, monolithium salt The title E compound (252.7 mg, 0.586 mmol, 1.0 eq.) was dissolved in methanol (1 ml, 0.60M) and treated with aqueous 1N lithium hydroxide (1.0 ml, 1.0 mmol, 1.7 eq.). The reaction was stirred at room temperature for 3 days and concentrated. The residue was dissolved in water and chromatographed on HP-20, eluting with water (100 ml), 2% acetone in water (75 ml), 5% acetone in water (75 ml), 10% acetone in water (100 ml), and 20% acetone in water (100 ml). The material was concentrated to a volume of approximately 50 ml and lyophilized. After obtaining carbon and proton NMR spectra, the product was dissolved in water (20 ml), filtered through a polycarbonate membrane and lyophilized to furnish 184.1 mg of the title compound.

EXAMPLE 3

5-[[2-Butyl-5-(hydroxymethyl)-1H-imidazol-1-yl]-methyl]-1-phenyl-1H-indole-2-carboxylic acid, monolithium salt A. 5-Methyl-1-phenyl-1H-indole-2-carboxylic acid, ethyl ester The title B indole of Example 1 (1.016 g, 5.0 mmol, 1.0 eq.) and bromobenzene (1.32 ml, 12.5 mmol, 2.5 eq.) were dissolved in pyridine (5 ml, 1M) and treated with copper(I) oxide (715 mg, 5.0 mmol, 1.0 eq.). The mixture was heated at 130° C. for a total of 5.5 hours. At 2.5 hours, additional bromobenzene (0.4 ml) and copper(I) oxide (215 mg) were added. After cooling, the mixture was diluted with ethyl acetate and filtered through Celite. The filtrate was washed with water (3×50 ml), 0.5N hydrochloric acid (2×50 ml) and saturated sodium hydrogen carbonate solution (50 ml), dried over anhydrous magnesium sulfate and freed of solvent in vacuo. The brown residue was chromatographed on silica gel eluting with 10% ether in hexane to give the title A compound (1.107 g). TLC: R$_f$=0.48, silica gel, ether:hexane (1:3).

B.

5-(Bromomethyl)-1-phenyl-1H-indole-2-carboxylic acid, ethyl ester

A mixture of the title A compound (1.105 g, 3.96 mmol, 1.0 eq.), N-bromosuccinimide (726 mg, 4.08 mmol, 1.03 eq.) and azobisisobutyronitrile (22 mg, 2% by weight) in carbon tetrachloride (40 ml, 0.1M) was heated in an oil bath maintained at 80°–90° C. for 75 minutes. The mixture was cooled to 0° C. The solid was removed by filtration and washed with cold carbon tetrachloride. The filtrate was taken to dryness in vacuo. The residue was chromatographed on silica gel eluting with 10% ether in hexane to give the title B compound (872 mg). TLC: R$_f$=0.42, silica gel, ether:hexane, 1:3.

C.

5-[(2-Butyl-5-formyl-1H-imidazol-1-yl)-methyl]-1-phenyl-1H-indole-2-carboxylic acid, ethyl ester The title H imidazole aldehyde of Example 1 (105 mg, 0.69 mmol, 1.15 eq.) was dissolved in distilled tetrahydrofuran (1.44 ml) and dimethylformamide (0.48 ml, 0.3M) in an argon atmosphere. The solution was cooled in an ice bath and a solution of potassium hexamethyl disilazane (0.7N in toluene, 1.03 ml, 0.72 mmol, 1.2 eq.) was added dropwise. The cooling bath was removed and the mixture was stirred 20 minutes. After again cooling in an ice bath, a solution of the title B compound (215 mg, 0.6 mmol, 1.0 eq.) in tetrahydrofuran (1 ml) was added and the mixture was allowed to warm slowly to room temperature and left stirring overnight. The reaction was quenched by adding saturated ammonium chloride solution. The product was extracted into ethyl acetate (3×30 ml). The combined extracts were dried over anhydrous magnesium sulfate and freed of solvent in vacuo. The remaining material was chromatographed on silica gel eluting with mixtures of acetone in toluene (1:15 followed by 1:12 followed by 1:10) to give the title C compound (251 mg). TLC: $R_f$=0.30, silica gel, acetone:toluene (1:4).

D.

5-[[2-Butyl-5-(hydroxymethyl)-1H-imidazol-1-yl]methyl]-1-phenyl-1H-indole-2-carboxylic acid, ethyl ester The title C compound (251 mg, 0.58 mmol, 1.0 eq.) was dissolved in ethanol (5.8 ml, 0.1M) and treated with a solution of sodium borohydride (22 mg, 0.58 mmol, 1.0 eq.) in ethanol (2 ml). The reaction was quenched after 75 minutes by adding 1N hydrochloric acid to pH 4. The solvent was removed in vacuo. Water was added and the solution was basified with solid sodium hydrogen carbonate. The product was extracted into ethyl acetate (3×20 ml), dried over anhydrous magnesium sulfate and freed of solvent in vacuo. The remaining material was chromatographed on silica gel eluting with hexane:acetone (1:1 followed by 1:2) containing 0.05% ammonium hydroxide to give the title D compound (219 mg). TLC: $R_f$=0.31, Silica gel, hexane:acetone (1:2)+ammonium hydroxide.

E.

5-[[2-Butyl-5-(hydroxymethyl)-1H-imidazol-1-yl]-methyl]-1-phenyl-1H-indole-2-carboxylic acid, monolithium salt The title D compound (218 mg, 0.507 mmol, 1.0 eq.) was dissolved in methanol (2.5 ml) and 1N lithium hydroxide solution (1.5 ml) was added causing material to precipitate. The cloudy mixture was stirred overnight at room temperature. The solvent was removed in vacuo. The residue was dissolved in water and applied to a column packed with HP-20 (20 ml). The column was eluted with water (~250 ml) until the eluate was neutral, then eluted with increasing amounts of acetone in water (100 ml of 5%, 100 ml of 10% and 100 ml of 15%). The product was eluted with 10 and 15% acetone. The fractions were combined and concentrated to a small volume in vacuo. After lyophilization, the material was used to obtain NMR spectra, recovered, dissolved in water, passed through a polycarbonate membrane and relyophilized to give the title compound (164 mg).

EXAMPLE 4

2-[4-[[2-Butyl-5-(hydroxymethyl)-1H-imidazol-1-yl]methyl]-1H-indol-1-yl]benzoic acid, monolithium salt

A.

2-[2-(2-Methyl-6-nitrophenyl)ethylidene]-hydrazinecarboxamide

3-Nitro-ortho-xylene (1.77 ml, 13.23 mmol, 1.0 eq.) was combined with dimethylformamide dimethyl acetal (2.11 ml, 15.88 mmol, 1.2 eq.) dimethylformamide (7.35 ml, 1.8M) and pyrrolidine (1.32 ml, 15.88 mmol, 1.2 eq.) and heated at 110° C. for 8 hours. The reaction was then cooled to room temperature and concentrated. The residue was dissolved in dimethylformamide (7.35 ml, 1.8M) and treated at room temperature with a solution of semicarbazide-hydrochloride (1.55 g, 13.89 mmol, 1.05 eq.) in concentrated hydrochloric acid (1.2 ml, 14.55 mmol, 1.1 eq.) and water (16.5 ml, 0.8M). The mixture was stirred at room temperature for 30 minutes, cooled to 0° C. and filtered. The precipitate was washed with water (30 ml), cold ethanol (15 ml) and ethyl ether (25 ml) and then dried in vacuo to provide the title A compound (2.44 g).

B.

4-Methyl-1H-indole

The title A compound (206.6 mg, 0.875 mmol, 1.0 eq.) was combined with ethanol (1.75 ml, 0.5M) and 10% palladium on carbon (41.3 mg, 20% by weight) and placed in a Parr shaker under a hydrogen atmosphere (60 psi) for 5 hours. The reaction was then diluted with methanol, filtered through regenerated cellulose and concentrated. The residue was chromatographed on Merck silica gel (5 g) eluting with chloroform:hexane (4:1) followed by (3:1) to provide the title B compound (101.7 mg).

C.

2-(4-Methyl-1H-indol-1-yl)benzoic acid, ethyl ester

The title B compound (101.5 mg, 0.774 mmol, 1.0 eq.) was combined with ortho-bromo-ethylbenzoate (443 mg, 1.93 mmol, 2.5 eq.) (as prepared in Example 1, compound C) and copper(I)oxide (132.9 mg, 0.928 mmol, 1.2 eq.) in pyridine (0.77 ml, 1M) and heated at 130° C. for 2 hours. The reaction was then cooled to room temperature, diluted with ethyl acetate, and filtered through celite. The filtrate was washed twice with water, twice with 1N hydrochloric acid, and once with saturated aqueous sodium hydrogen carbonate. The solution was then dried over sodium sulfate, filtered through magnesium sulfate and concentrated. The residue was chromatographed on Merck silica gel (10 g) eluting with toluene: hexane (1:2) followed by ether:hexane (1:10). The product was then rechromatographed on Merck silica gel (10 g) eluting with ether:hexane (1:40) followed by (1:10) to furnish the title C compound (154 mg).

D.

2-[3-(or 2,3-Di)bromo-4-(bromomethyl)-1H-indol-1-yl]benzoic acid, ethyl ester

The title C compound (146.8 mg, 0.526 mmol, 1.0 eq.) was combined with N-bromosuccinimide (188.9 mg, 1.06 mmol, 2.02 eq.) and azobisisobutyronitrile (4.4 mg, 3% by weight, Chemical Dynamics Corp.) in carbon tetrachloride (8.8 ml, 0.06M) and heated at 60° C. for 30 minutes. A drop of the mixture gave a negative starch-potassium iodide test at this time. The reaction was then cooled to 0° C., filtered and concentrated. The residue was chromatographed on Merck silica gel (10 g) eluting with ether:hexane (1:40) followed by (1:10) to give the title D compound (112.7 mg) as a mixture of di- and tri-bromides.

E.

2-[3-(or 2,3-Di)bromo-4-[(2-butyl-5-formyl-1H-imidazol-1-yl)methyl]-1H-indol-1-yl]-benzoic acid, ethyl ester The title D compound (112.7 mg, 0.258 mmol, 1.0 eq.) was combined with the title H compound of Example 1 (43.2 mg, 0.284 mmol, 1.1 eq.) and dissolved in t-butanol (0.52 ml, 0.5M) and tetrahydrofuran (0.26 ml, 1M). The solution was then treated with potassium t-butoxide (36.5 mg, 0.309 mmol, 1.2 eq.) and stirred at room temperature for 4 hours. More t-butanol (0.26 ml) was added and the reaction was heated at 60° C. for 30 minutes. The solution was cooled to room temperature, quenched with aqueous saturated ammonium chloride and water, and extracted three times with ethyl acetate. The organic extracts were dried over sodium sulfate, filtered through magnesium sulfate and concentrated. The residue was chromatographed on Merck silica gel (5 g) eluting with toluene: acetone (12:1) to provide the title E compound (128 mg).

F.

2-[3-(or 2,3-Di)bromo-4-[[2-butyl-5-(hydroxymethyl)-1H-imidazol-1-yl]methyl]-1H-indol-1-yl]benzoic acid, ethyl ester The title E compound (123.3 mg, 0.242 mmol, 1.0 eq.) was dissolved in ethanol (2.4 ml, 0.1M) and treated at room temperature with sodium borohydride (9.2 mg, 0.242 mmol, 1.0 eq.) dissolved in ethanol (0.92 ml). The reaction was stirred at room temperature for 1 hour, quenched with 1N hydrochloric acid and concentrated. Saturated aqueous sodium hydrogen carbonate was added to the residue and the aqueous mixture was extracted three times with ethyl acetate. The organic extracts were filtered through magnesium sulfate and concentrated. The residue was chromatographed on Merck silica gel (5 g) eluting with chloroform:methanol:ammonium hydroxide (30:0.8:0.05) to furnish the title F compound (125.2 mg).

G.

2-[4-[[2-Butyl-5-(hydroxymethyl)-1H-imidazol-1-yl]methyl]-1H-indol-1-yl]benzoic acid, ethyl ester The title F compound (117.4 mg, 0.230 mmol, 1.0 eq.) was combined with palladium hydroxide on carbon (23.5 mg, 20% by weight), triethylamine (0.10 ml, 0.690 mmol, 3.0 eq.) and ethanol (4.6 ml, 0.05M) and placed under a balloon of hydrogen gas for 45 minutes. The reaction was then diluted with ethanol, filtered through regenerated cellulose and concentrated. The residue was chromatographed on Merck silica gel (5 g) eluting with chloroform:methanol:ammonium hydroxide (30:0.7:0.05) to provide the title G compound (65.2 mg).

H.

2-[4-[[2-Butyl-5-(hydroxymethyl)-1H-imidazol-1-yl]methyl]-1H-indol-1-yl]benzoic acid, monolithium salt The title G compound (65.2 mg, 0.151 mmol, 1.0 eq.) was dissolved in methanol (1 ml) and aqueous 1N lithium hydroxide (1 ml). The reaction was stirred at room temperature for 3 days and concentrated. The residue was chromatographed on HP-20 resin (10 g) eluting with water (100 ml), 5% acetone in water (80 ml), 10% acetone in water (80 ml), 20% acetone in water (80 ml), and 35% acetone in water (80 ml). The product eluted between 10% and 35%. The fractions were concentrated to a volume of ~25 ml and lyophilized. After obtaining NMR spectra, the product was dissolved in water (15 ml), filtered through a polycarbonate membrane and lyophilized to furnish the title compound (64.7 mg).

EXAMPLE 5

5-[[2-Butyl-4-chloro-5-(hydroxymethyl)-1H-imidazol-1-yl]methyl]-1-[2-(1H-tetrazol-5-yl)phenyl]-2H-indole-2-carboxylic acid, dilithium salt

A.

1-(2-Cyanophenyl)-5-methyl-1H-indole-2-carboxylic acid, ethyl ester

A mixture of the title B compound from Example 1 (2.027 g, 9.975 mmol, 1.0 eq., prepared as described in Example 1, part B), powdered potassium carbonate (2.76 g, 19.95 mmol, 2.0 eq.), 2-fluorobenzonitrile (2.71 ml, 24.9 mmol, 2.5 eq.) and 18-crown-6 (263 mg, 0.99 mmol, 0.1 eq.) in dimethylformamide (20 ml, 0.5M) was stirred and heated in an oil bath maintained at 150±5° C. Additional 2-fluorobenzonitrile (1.1 ml, 9.975 mmol, 1.0 eq.) was added after 3.5 hours and 18-crown-6 (263 mg, 0.1 eq.) after 18 hours. After heating 28 hours the mixture was cooled, diluted with water and extracted with ether:hexane (1:1, 3×100 ml). The combined extracts were washed once with water and once with saturated sodium chloride solution, dried over anhydrous magnesium sulfate and freed of solvent in vacuo. The product was purified by chromatography on silica gel (150 g), eluting fast-moving impurities with toluene:hexane (2:1) and then the desired product was eluted with toluene to give the title A compound (1.88 g). TLC: $R_f=0.41$, silica gel, 5% ethyl acetate in toluene, UV.

B.

5-(Bromomethyl)-1-(2-cyanophenyl)-1H-indole-2-carboxylic acid, ethyl ester

The title A compound (1.88 g, 6.17 mmol, 1.0 eq.) was dissolved in carbon tetrachloride (62 ml, 0.1M) and treated with N-bromosuccinimide (1.13 g, 6.36 mmol, 1.03 eq.) and azobisisobutyronitrile (38 mg, 2% by weight, Chemical Dynamics Corp.). The mixture was heated under reflux 5 hours. A drop of the mixture gave a negative starch-potassium iodide test at this time. After cooling in an ice bath, the solid was removed by filtration and washed with cold carbon tetrachloride. The filtrate was taken to dryness in vacuo. The remaining material was chromatographed on silica gel (180 g). Fast-moving impurities were eluted with 5% acetone in hexane. The desired bromo compound was then eluted with 10% acetone in hexane to give the title B compound (1.54 g). (TLC: $R_f$=0.29, silica gel, 20% acetone in hexane, UV).

C.

2-Butyl-4-chloro-5-formyl imidazole

A solution of the title G compound of Example 1 (6.15 g, 39.9 mmol) in a mixture of absolute ethanol (40 ml) and tetrahydrofuran (80 ml) was cooled in an ice bath. To the cold solution was added N-chlorosuccinimide (5.9 g, 44.4 mmol) in small portions over 60 minutes. The resulting mixture was stirred for 30 minutes in the ice bath, then for 30 minutes at 25° C., after which a starch-iodine test was negative. The mixture was concentrated in vacuo to give a residue which was triturated with ether (400 ml) to give a tan solid. The mother liquor from trituration was concentrated and the residue was re-triturated with ether (40 ml) to give more of the tan solid. The solids were combined, dissolved in pyridine (200 ml), and warmed to 100° C. Manganese dioxide (20 g) was added to the warm solution and the resulting black mixture was stirred at 100° C. for one hour. The hot solution was filtered and concentrated. The residue was purified by chromatography on silica gel (500 g), eluting with 3:1 hexane:ethyl acetate, to give a major product having $R_f$ 0.4. The product was triturated with petroleum ether to give the title C compound as a white crystalline solid (3.9 g), m.p. 96°–97° C.

D.

5-[(2-Butyl-4-chloro-5-formyl-1H-imidazol-1-yl)methyl]-1-(2-cyanophenyl)-1H-indole-2-carboxylic acid, ethyl ester A solution of the title B compound (1.16 g, 3.026 mmol, 1 eq.) and the title C compound (621 mg, 3.33 mmol, 1.1 eq.) in dimethylformamide (15.1 ml, 0.2M) in an argon atmosphere was treated with potassium t-butoxide (462 mg, 3.78 mmol, 1.25 eq.) and 18-crown-6 (160 mg, 0.6 mmol, 0.2 eq.) and the mixture was stirred at room temperature for 27 hours. The reaction was quenched with saturated ammonium chloride solution and diluted with water. The product was extracted into ethyl acetate (3×50 ml), dried over anhydrous magnesium sulfate and freed of solvent in vacuo. The remaining material was chromatographed on silica gel (120 g). Unreacted imidazole starting material was eluted with 10% acetone in hexane. The desired product was eluted with 20% acetone in hexane to give the title D compound (815 mg). TLC: $R_f$=0.34, silica gel, 30% acetone in hexane, UV.

E.

5-[[2-Butyl-4-chloro-5-(hydroxymethyl)-1H-imidazol-1-yl)methyl]-1-(2-cyanophenyl)-1H-indole-2-carboxylic acid, ethyl ester The title D compound (815 mg, 1.67 mmol, 1 eq.) was dissolved in ethanol (17 ml, 0.1M) and treated with a solution of sodium borohydride (63 mg, 1.67 mmol, 1 eq.) in ethanol (5 ml). The mixture was stirred at room temperature one hour, then acidified to pH 4 with 1N hydrochloric acid and stirred at room temperature 30 minutes. The solvent was removed in vacuo. Dilute sodium bicarbonate was added and the product was extracted into ethyl acetate (3×50 ml). The combined organic extracts were dried over anhydrous magnesium sulfate and freed of solvent in vacuo. The residue was chromatographed on silica gel (70 g). Less polar impurities were eluted with ether:hexane (1:1 followed by 2:1). The desired alcohol was eluted with ether to give the title E compound (569 mg). TLC: $R_f$=0.48, silica gel, ethyl ether, UV.

F.

5-[[2-Butyl-4-chloro-5-(hydroxymethyl)-1H-imidazol-1-yl]methyl]-1-[2-(2H-tetrazol-5-yl)phenyl]-1H-indole-2-carboxylic acid, ethyl ester The title E compound (72.2 mg, 0.1429 mmol, 1.0 eq.) and tributyl tin azide (71.2 mg, 0.214 mmol, 1.5 eq.) were dissolved in xylene (1.4 ml, 0.1M) and heated in an oil bath maintained at 140°–150° C. Additional tributyl tin azide (47.5 mg, 0.1429 mmol, 1 eq.) was added after 6 hours and heating was continued for a total of 12 hours. After cooling, the solvent was removed in vacuo and the remaining material was chromatographed on silica gel (13 g) eluting with 3% methanol in dichloromethane containing 0.2% acetic acid, followd by 5% methanol in dichloromethane with 0.2% acetic acid to give the title F compound (55 mg). TLC: $R_f$=0.28, silica gel, 7% methanol in dichloromethane containing acetic acid (2 drops/10 ml), UV.

G.

5-[[2-Butyl-4-chloro-5-(hydroxymethyl)-1H-imidazol-1-yl]methyl]-1-[2-(1H-tetrazol-5-yl)phenyl]-2H-indole-2-carboxylic acid, dilithium salt The title F compound (55 mg, 0.102 mmol, 1.0 eq.) was dissolved in methanol (1 ml) and treated with 1N lithium hydroxide solution (1 ml). The mixture was stirred at room temperature 20 hours. The solvent was removed in vacuo. The remaining material was combined with that obtained from a similar reaction run on a 0.04 mmol scale and purified on a column packed with 12 ml of HP-20 resin. The column was first eluted with water, then with 2% acetone in water. The desired material started eluting after ~50 ml of water had been passed through the column and the elution was accelerated when the acetone was added. The fractions containing the product were combined, concentrated to a small volume and lyophilized. This was used to obtain NMR spectra, recovered, dissolved in water (10 ml), passed through a polycarbonate filter and relyophilized to give the title compound (55.0 mg).

EXAMPLE 6

5-[[2-Butyl-4-chloro-5-(hydroxymethyl)-1H-imidazol-1-yl]methyl]-1-[2-(2H-tetrazol-5-yl)phenyl]-1H-indole-2-carboxylic acid, ethyl ester, monosodium salt The title F compound from Example 5 (82 mg, 0.153 mmol, 1 eq.) was dissolved in methanol (5 ml) and treated with 1N sodium hydrogen carbonate solution (0.31 ml, 2.0 eq.). The mixture was stirred a few minutes at room temperature, then taken to dryness in vacuo. The residue was applied to a column packed with HP-20 resin (10 ml). The column was eluted first with water, then with increasing amounts of acetone in water in 5% increments. The product was eluted with 15 and 20% acetone in water. Fractions containing the product were combined and lyophilized. This was used to obtain NMR spectra, recovered, dissolved in water (10 ml), passed through a polycarbonate membrane and relyophilized to give the title compound (63.5 mg).

EXAMPLE 7

2-Butyl-4-chloro-1-[[1-[2-(2H-tetrazol-5-yl)phenyl]-1H-indol-4-yl]methyl]-1H-imidazole-5-methanol, monolithium salt

A.

1-(2-Cyanophenyl)-4-methyl-1H-indole

The title B compound of Example 4 (1.042 g, 7.94 mmol, 1.0 eq.) was combined with 2-fluorobenzonitrile (1.29 ml, 11.91 mmol, 1.5 eq.) and potassium carbonate (2.195 g, 15.88 mmol, 2.0 eq.) in dimethylformamide (7.94 ml, 1M) and heated at 150° C. for 4 hours. The reaction was then cooled to room temperature, diluted with water (20 ml), and extracted three times with ethyl acetate. The organic extracts were washed with water and aqueous saturated sodium chloride, dried over sodium sulfate, filtered through magnesium sulfate and concentrated. The residue was chromatographed on Merck silica gel (50 g) eluting with chloroform:hexane (1:3) followed by (1:1) to give the title A compound (1.57 g).

B.

2-[3-(or 2,3-Di)bromo-4-(bromomethyl)-1H-indol-1-yl]benzonitrile

N-bromosuccinimide (3.615 g, 20.11 mmol, 3.0 eq.) was added to a solution of the title A compound (1.557 g, 6.70 mmol, 1.0 eq.) in carbon tetrachloride (134 ml, 0.05M) and benzene (26.8 ml, 0.25M) and the reaction was placed next to a bright lamp at room temperature for 3 hours. The mixture was then diluted with chloroform (134 ml, 0.05M), cooled to 0° C., filtered and concentrated. The residue was chromatographed on Merck silica gel (100 g) eluting with hexane:chloroform (1:1) followed by (2:3) followed by (1:2) to give the title B compound (2.268 g).

C.

2-[3-(or 2,3-Di)bromo-4-[(2-butyl-4-chloro-5-formyl-1H-imidazol-1-yl)methyl]-1H-indol-1-yl]benzonitrile The title B compound (2.268 g, 4.84 mmol, 1.0 eq.) was combined with the title C compound from Example 5 (993 mg, 5.32 mmol, 1.1 eq.) and dissolved in t-butanol (9.7 ml, 0.5M) and dimethylformamide (9.7 ml, 0.5M). The solution was then treated with potassium t-butoxide (671 mg, 5.80 mmol, 1.2 eq.), and heated at 60° C. for 90 minutes. The reaction was then cooled to room temperature diluted with water (40 ml) and extracted with ethyl acetate (3×30 ml). The organic extracts were next washed with water (20 ml) and aqueous saturated sodium chloride (20 ml), dried over sodium sulfate, filtered through magnesium sulfate and concentrated. The residue was chromatographed on Merck silica gel (100 g) eluting with toluene: ethyl acetate (25:1) to give the title C compound (1.865 g).

D.

2-[3-(or 2,3-Di)bromo-4-[[2-butyl-4-chloro-5-(hydroxymethyl)-1H-imidazol-1-yl]methyl]-1H-indol-1-yl]benzonitrile The title C compound (1.865 g, 3.24 mmol, 1.0 eq.) was dissolved in ethanol (32.4 ml, 0.1M) and treated at room temperature with sodium borohydride (124 mg, 3.24 mmol, 1.0 eq.) dissolved in ethanol (12.4 ml). The reaction was stirred at room temperature for 1 hour, quenched with 1N hydrochloric acid and concentrated. Saturated aqueous sodium hydrogen carbonate and water were added to the residue and the aqueous mixture was extracted three times with ethyl acetate. The organic extracts were dried over sodium sulfate, filtered through magnesium sulfate and concentrated. The residue was chromatographed on Merck silica gel (50 g) eluting with chloroform:ether (10:1) followed by (5:1) to give the title D compound (1,638 g).

E.

2-[4-[[2-Butyl-4-chloro-5-(hydroxymethyl)-1H-imidazol-1-yl]methyl]-1H-indol-1-yl]-benzonitrile The title D compound (1.638 g, 2.84 mmol, 1.0 eq.) was combined with palladium hydroxide on carbon (328 mg, 20% by weight), triethylamine (1.19 ml, 8.52 mmol, 3.0 eq.) and ethanol (56.8 ml, 0.05M) and placed under a balloon of hydrogen gas for 45 minutes. The reaction was then diluted with methanol (60 ml), filtered through regenerated cellulose and concentrated. The residue was chromatographed on Merck silica gel (35 g) eluting with chloroform:ethyl acetate (4:1) to give the title E compound (1,188 g).

F.

2-Butyl-4-chloro-1-[[1-[2-(2H-tetrazol-5-yl)phenyl]-1H-indol-4-yl]methyl]-1H-imidazole-5-methanol The title E compound (1.119 g, 2.67 mmol, 1.0 eq.) and tributyl tin azide (2.218 g, 6.68 mmol, 2.5 eq.) were dissolved in xylene (10.7 ml, 0.25M) and heated at 150° C. for 5 hours. The reaction was then cooled to room temperature and concentrated. The residue was chromatographed on Merck silica gel (75 g)eluting with chloroform: methanol:acetic acid (30:1.5:0.05) followed by (30:3:0.05) to furnish the title F compound (940 mg).

G.

2-Butyl-4-chloro-1-[[1-[2-(2H-tetrazol-5-yl)-phenyl]-1H-indol-4-yl]methyl]-1H-imidazole-5-methanol, monolithium salt The title F compound (940 mg, 2.03 mmol, 1.0 eq.) was dissolved in methanol (10 ml, 0.2M) and aqueous 1N lithium hydroxide (10 ml, 0.2M). The reaction was stirred at room temperature for 30 minutes and concentrated. The residue was chromatographed on HP-20 resin (50 g) eluting with water (400 ml), 5% acetone in water (400 ml), 10% acetone in water (400 ml), 20% acetone in water (400 ml) and 30% acetone in water (400 ml). The product eluted between 20% and 30%. The fractions were concentrated to a volume of ~50 ml and lyophilized. After obtaining NMR spectra, the product was dissolved in water (50 ml), filtered through a polycarbonate membrane and lyophilized to furnish the title compound (708 mg).

EXAMPLE 8

2-Butyl-4-chloro-1-[[1-[2-(2H-tetrazol-5-yl)-phenyl]-1H-benzimidazol-4-yl]methyl]-1H-imidazole-5-methanol, monolithium salt

A.

4-Methyl-1H-benzimidazole 2,3-Diaminotoluene (675 mg, 5.53 mmol) was dissolved in 10 mL of dry tetrahydrofuran and triethylamine (0.77 mL, 5.53 mmol) was added. The mixture was cooled to 0° and 1,1-dichloromethyl methyl ether (0.50 mL, 5.53 mmol) was added and the reaction was allowed to warm to room temperature. After 20 hours, the reaction was quenched with sodium bicarbonate. The aqueous phase was extracted with ethyl acetate, dried over magnesium sulfate, filtered and the solvent removed to yield 730 mg of the title A compound as a brown solid that was used in the next reaction without purification.

B.

2-(4-Methyl-1H-benzimidazol-1-yl)-benzonitrile

The title A compound (133 mg, 1.01 mmol), 2-fluorbenzonitrile (164 μL, 1.51 mmol) and finely ground potassium carbonate (279 mg, 2.02 mmol) were combined in 1 mL of N,N-dimethylformamide and heated to 80°. After stirring for 20 hours, the dimethylformamide was removed in vacuo and the brown solid residue was partitioned between saturated sodium bicarbonate and ethyl acetate. The aqueous phase was extracted with ethyl acetate and the combined organic extracts were dried over magnesium sulfate, filtered and the solvent removed. The residue was purified by flash chromatography (20 g silica gel, eluted with ethyl acetate, hexane) to provide 160 mg of the title B compound as a white solid.

C.

2-[4-(Bromomethyl)-1H-benzimidazol-1-yl]-benzonitrile

The title B compound (71 mg, 0.30 mmol) was dissolved in 5 mL of 50% carbon tetrachloride and benzene. Azobisisobutyronitrile (10 mg, 0.06 mmol) and N-bromosuccinimide (65 mg, 0.36 mmol) were added and the mixture was heated to 75° for 4 hours. The solvent was removed and the residue was purified by flash chromatography (20 g silica gel eluted with 10% acetone, toluene) to yield 79 mg of the title C compound as a white solid, m.p. 135° C. (dec).

D.

2-[4-[(2-Butyl-4-chloro-5-formyl-1H-imidazole-1-yl)methyl]-1H-benzimidazol-1-yl]benzonitrile The title C compound (1.296 g, 4.15 mmol) and 2-butyl-4-chloro-1H-imidazole-5-carboxaldehyde (949 mg, 4.15 mmol) (prepared as in Example 5, compound C) were dissolved under argon in 20 mL of dichloromethane. 1,8-Diazabicyclo[5.4.0]undec-7-ene (0.621 mL, 4.15 mmol) was added and the reaction was allowed to stir for 15 hours at room temperature. The solvent was then removed in vacuo and the orange oil residue was purified by flash chromatography (145 g silica gel; 10% acetone, toluene) to yield 1.0563 g of the title D compound as a yellow solid, m.p. 117°–135°.

E.

2-[4-[[2-Butyl-4-chloro-5-(hydroxymethyl)-1H-imidazol-1-yl]methyl]-1H-benzimidazol-1-yl]benzonitrile The title D compound (757 mg, 1.81 mmol) was suspended in 8 mL of ethanol and sodium borohydride (69 mg, 1.81 mmol) was added. The reaction was stirred at room temperature for 50 minutes at which time all of the solid had dissolved. The ethanol was removed and the residue (yellow oil) was partitioned between ethyl acetate and 1N sodium hydroxide. The aqueous phase was extracted with ethyl acetate and the combined organic extracts were dried over magnesium sulfate, filtered and the solvent removed. The residue was purified by flash chromatography (110 g silica gel; 7% isopropanol, toluene) to give 675 mg of the title E compound as a white solid.

F.

2-Butyl-4-chloro-1-[[1-[2-(2H-tetrazol-5-yl)phenyl]-1H-benzimidazol-4-yl]methyl]-1H-imidazole-5-methanol, monolithium salt The title E compound (600 mg, 1.42 mmol) and tributyl tin azide (949 mg, 2.86 mmol) were dissolved in 4 mL of xylenes under argon and heated to 110° for 20 hours. The xylenes were removed in vacuo to yield a brown oil that was purified by flash chromatography (165 g silica gel; 5% acetic acid, 5% methanol, 50% toluene, 40% ethyl acetate) to yield an oil with an insoluble white precipitate. This residue was dissolved in methanol and filtered to give494 mg of a brown oil. This oil was dissolved in 2 mL of 1N lithium hydroxide and purified by column chromatography (100 mL HP-20 resin eluted with 100 mL each of water to 45% acetone in 5% increments) to yield 255 mg of the title compound as a fluffy white solid, m.p. 240°–270° C.

EXAMPLE 9

2-Butyl-4-chloro-1-[[1-[2-(2H-tetrazol-5-yl)-phenyl]-1H-indol-4-yl]methyl]-1H-imidazole-5carboxylic acid, dilithium salt

A.

2-[2,3-Dibromo-4-(bromomethyl)-1H-indol-1-yl]benzonitrile 2-(4-Methyl-1H-indol-1-yl)benzonitrile (2.323 g, 0.01 mol, 1 eq) (prepared as in Example 7, compound A) in 200 ml carbon tetrachloride and 40 ml benzene at room temperature, added the N-bromosuccinimide (5.340 g, 0.03 mol, 3 eq) and placed next to a bright lamp. Stirred at room temperature for a total of 5 hours. At 3 hours and 4 hours, additional N-bromosuccinimide (0.534 g, 0.003 mol, 0.3 eq, and 0.277 g, 0.0015 mol, 0.15 eq) was added. Methylene chloride (200 ml) was added and the reaction mixture was cooled to 0° C. and filtered. The filtrate was concentrated and the residue was chromatographed on silica gel eluting with hexane:methylene chloride (1:1) to give the title A compound (3.28 g). TLC: $R_f$=0.65, Toluene: ethyl acetate (10:1), UV.

B.

2-[2,3-Dibromo-4-[(2-butyl-4-chloro-5-formyl-1H-indol-1-yl)methyl]-1H-indol-1-yl]benzonitrile To the solution of 2-butyl-4-chloro-1H-imidazole-5-carboxaldehyde (679 mg, 3.636 mmol, 1.1 eq) (prepared as in Example 5, compound C) in t-BuOH-DMF (1:1, 13.2 ml, 0.25M) was added t-BuOK (445 mg, 3.966 mmol, 1.2 eq) and the mixture was stirred at room temperature for 25 minutes. Solid title A compound (1550 mg, 3.305 mmol, 1 eq) was then added. After stirring at room temperature for 5 hours, the mixture was added to 30 ml water and extracted with methylene chloride (30 ml×3). The extracts were washed with water (10 ml) and saturated sodium chloride (10 ml), dried over magnesium sulfate, filtered and concentrated. The residue was chromatographed on silica gel eluting with methylene chloride:ethyl acetate (100:1) to give the title B compound (1335 mg). TLC: $R_f$=0.4, Toluene: ethyl acetate (10:1), UV.

C.

2-Butyl-4-chloro-1-[[1-(2-cyanophenyl)-1H-indol-4-yl]methyl]-1H-imidazole-5-carboxylic acid To the title B compound (1455 mg, 2.532 mmol, 1 eq) and sulfamic acid (860 mg, 8.862 mmol, 3.5 eq) in tetrahydrofuran (24 ml, 0.1M) at 0° C., added sodium chlorite (801 mg, 8.862 mmol, 3.5 eq) in water (24 ml, 0.1M) dropwise. After stirring at 0° C. for 30 minutes, 30 ml methylene chloride was added into the reaction. The aqueous layer was extracted with methylene chloride (30 ml×3). The organic extracts were washed with water and dried over magnesium sulfate, and concentrated to give 2-butyl-4-chloro-1-[[2,3-dibromo-1-(2-cyanophenyl)-1H-indol-4-yl]-methyl]-1H-imidazole-5-carboxylic acid.

To 2-butyl-4-chloro-1-[[2,3-dibromo-1-(2-cyanophenyl)1H-indol-4-yl]-methyl]-1H-imidazole-5-carboxylic acid in ethanol (50.6 ml, 0.05M), added 1N sodium hydroxide (8.86 ml, 8.86 mmol, 3.5 eq) and palladium hydroxide on carbon (299 mg, 20% by weight). The reaction was placed under a balloon of hydrogen gas for 1 hour and 15 minutes. At 45 minutes, additional palladium hydroxide on carbon (100 mg, 6.7% by weight) was added. Water (50 ml) and methylene chloride (200 ml) were added, and the reaction was filtered. 1N Hydrogen chloride was added to the filtrate until pH 4–5. The aqueous layer was extracted with methylene chloride. The organic extracts were washed with saturated sodium chloride, dried over anhydrous magnesium sulfate and concentrated. The residue was chromatographed on silica gel eluting with methylene chloride:methanol:acetic acid (100:2:0.1) to give the title C compound (940 mg). TLC: $R_f$=0.3, ethyl acetate: methanol (5:1), UV.

D.

2-Butyl-4-chloro-1-[[1-[2-(2H-tetrazol-5-yl)phenyl]-1H-indol-4-yl]methyl]-1H-imidazole-5-carboxylic acid, dilithium salt A mixture of the title C compound (916 mg, 2.116 mmol, 1 eq), Bu$_3$SnN$_3$ (2108 mg, 6.348 mmol, 3 eq) and xylene (26.45 ml, 0.08M) was heated at 120° C. for 49 hours. After cooling to room temperature, methanol (13.2 ml) and acetic acid (0.485 ml, 4 eq) were added and the mixture was stirred at room temperature for 3 days. The mixture was concentrated and the residue was chromatographed on silica gel eluting with ethyl acetate:pyridine:acetic acid:water (40:1:1:0.5) to give 2-butyl-4-chloro-1-[[1-[2-(2H-tetrazol-5-yl)phenyl]-1H-indol-4-yl]methyl]-1H-imidazole-5-carboxylic acid.

2-Butyl-4-chloro-1-[[1-[2-(2H-tetrazol-5-yl)phenyl]-1H-indol-4-yl]methyl]1H-imidazole-5-carboxylic acid was dissolved in methanol (20 ml, 0.1M). A solution of lithium hydroxide in water (1N, 5.29 ml, 5.29 mmol, 2.5 eq) was added. After stirring at room temperature for 0.5 hours, most solvent of the reaction was evaporated under vacuum. The residue was chromatographed on HP-20 eluting with acetone in water (5–15%) to give the title compound (472 mg). TLC: $R_f$=0.31, ethyl acetate:pyridine:acetic acid:water (10:1:1:0.5), UV.

EXAMPLE 10

2-Butyl-4-chloro-1-[[1-[2-(2H-tetrazol-5-yl)-phenyl]-benzimidazol-4-yl]methyl]-1H-imidazole-5-carboxylic acid, dilithium salt

A.

2-Butyl-4-chloro-1-[[1-(2-cyanophenyl)-1H-benzimidazol-4-yl]methyl]-1H-imidazole-5-carboxaldehyde 2-[4-(Bromomethyl)-1H-benzimidazol-1-yl]-benzonitrile (0.65 g, 2.08 mmol, prepared as described in part C of Example 8) and 2-butyl-4-chloro-1H-imidazole-5-carboxaldehyde (0.409 g, 2.19 mmol, prepared as described in part C of Example 5) were placed in 20.8 mL anhydrous dimethylformamide. Freshly ground cesium carbonate (1.02 g, 3.12 mmol) was then added and the reaction was stirred at room temperature for 16 hours. The reaction was then partitioned between ethyl acetate and water and the organic phase was washed with brine, dried and concentrated. The crude oil was purified by flash chromatography (SiO$_2$, 80:20 hexane:acetone) to yield the title A compound (0.68 g) as a white solid.

B.

2-Butyl-4-chloro-1-[[1-(2-cyanophenyl)-1H-benzimidazol-4-yl]methyl]-1H-imidazole-5-carboxylic acid The title A compound (0.636 g, 1.52 mmol) and sulfamic acid (0,369 g, 3.80 mmol) were dissolved in 10.0 mL of dry tetrahydrofuran and the solution was then cooled to 0° C. A solution of sodium chlorite (0.361 g, 4.0 mmol) in 4.0 mL of water was then added and the reaction was allowed to stir at 0° C. for 45 minutes. The reaction was partitioned between methylene chloride and water and the organic phase was dried and concentrated. The crude oil was purified by flash chromatography (SiO$_2$, 60:25:10:5 acetone: hexane:methanol:acetic acid) to provide the title B compound (0.474 g).

C.

2-Butyl-4-chloro-1-[[1-[2-(2H-tetrazol-5-yl)phenyl]-1H-benzimidazol-4-yl]methyl]-1H-imidazole-5-carboxylic acid The title B compound (0.462 g, 1.06 mmol) and tributyltin azide (1.41 g, 4.24 mmol) were combined in 6.0 mL of xylene and reaction was heated to 100° C. for 18 hours. The reaction was then concentrated to half of the original volume and heated for another 18 hours. The reaction was then concentrated and purified by flash chromatography (SiO$_2$, 70:23:7 toluene:acetone:acetic acid) to provide the title C compound (0.450 g).

D.

2-Butyl-4-chloro-1-[[1-[2-(2H-tetrazol-5-yl)phenyl]benzimidazol-4-yl]methyl]-1H-imidazole-5-carboxylic acid, dilithium salt To the title C compound (0.435 g, 0.912 mmol) was added 2.1 mL of 1.0M lithium hydroxide in water. Another 7 mL of water and 0.5 mL of methanol were added in order to effect a solution. The solution was then purified using an HP-20 column, eluting with 500 mL each of water to 20% methanol: 80% water in 2% increments. The product was collected, passed through a millipore filter, and lyophilized to provide the title compound (0.377 g) as a white solid, m.p.>280° C.

EXAMPLE 11

2-Butyl-4-chloro-1-[[1-[2-(2H-tetrazol-5-yl)phenyl]-1H-indol-4-yl]methyl]-1H-imidazole-5-carboxylic acid, butyl ester, monopotassium salt

A.

2-Butyl-4-chloro-1-[[1-(2-cyanophenyl)-1H-indol-4-yl]methyl]-1H-imidazole-5-carboxylic acid, butyl ester 2-Butyl-4-chloro-1-[[1-(2-cyanophenyl)-1H-indol-4-yl]methyl]-1H-imidazole-5-carboxylic acid (661 mg, 1.527 mmol, 1 eq. prepared as described in part C of Example 9) and n-butyl iodide (562 mg, 3.054 mmol, 2 eq.) in dimethylformamide (3.05 ml, 0.5M) under argon, cesium carbonate (1244 mg, 3.818 mmol, 2.5 eq.) was added. The reaction was stirred at room temperature for 2.5 hours. Ethyl acetate was added and the mixture was filtered. The filtrate was washed with pH ~4 buffer, and saturated sodium chloride, dried over anhydrous magnesium sulfate and concentrated. The residue was chromatographed on silica gel eluting with Hexane:ethyl acetate (5:1) to give the title A compound (671 mg). TLC: $R_f$=0.21, Hexane:ethyl acetate (3:1).

B.

2-Butyl-4-chloro-1-[[1-[2-(2H-tetrazol-5-yl)phenyl]-1H-indol-4-yl]methyl]-1H-imidazole-5-carboxylic acid, butyl ester, monopotassium salt A mixture of the title A compound (693 mg, 1.417 mmol, 1 eq.), tributyltin azide (2.353 g, 7.086 mmol, 5 eq.) and xylene (1 ml) was heated at 100° C. overnight. The reaction mixture was chromatographed on silica gel eluting with Hexane: ethyl acetate:acetic acid (100:8~15:1) and then Hexane:ethyl acetate:acetic acid (60:40:1) to give 2-butyl-4-chloro-1-[[1-[2-(2H-tetrazol-5-yl)phenyl]-1H-indol-4-yl]methyl]-1H-imidazole-5-carboxylic acid.

2-Butyl-4-chloro-1-[[1-[2-(2H-tetrazol-5-yl)phenyl]-1H-indol-4-yl]methyl]-1H-imidazole-5-carboxylic acid was dissolved in methanol (28 ml, 0.05M) and potassium hydrogen carbonate water solution (1N, 1.84 ml, 1.84 mmol, 1.3 eq.) was added. The mixture was stirred at room temperature for 20 minutes. 10 ml Water was added and part of the solvent was evaporated under vacuum. The residue was chromatographed on a HP-20 column eluting with water, followed by water: acetone (100:25~40) to give the title compound (581 mg).

EXAMPLE 12

2-Butyl-4-chloro-1-[[2,3-dibromo-1-[2-(1H-tetrazol-5-yl)phenyl]1H-indol-4-yl]methyl]-1H-imidazole-5-carboxylic acid, dilithium salt 2-Butyl-4-chloro-1-[[2,3-dibromo-1-(2-cyanophenyl)-1H-indol-4-yl]methyl]-1H-imidazole-5-carboxylic acid (0.3 g, 0.51 mmol, prepared as described in part C of Example 9) and tributyltin azide (0.51 g, 1.5 mmol) were dissolved in 0.3 ml of toluene and heated at 80° C. for 15 hours. The crude reaction mixture was chromatographed directly through 80 g of Merck silica gel using a (60:40:0.2) hexane:ethyl acetate:acetic acid solvent system. The appropriate fractions were combined, concentrated in vacuo and dissolved in 4 ml of (1:1) methanol: 1N lithium hydroxide. This material was chromatographed through 80 ml of HP-20 using an aqueous system containing 15% acetone. The appropriate fractions were combined, concentrated to 100 ml, filtered through millipore, and lyophilized. The lyophilate was dried over $P_2O_5$ to give the title compound (0.24 g) as a white solid.

EXAMPLE 13

2-Butyl-4-chloro-1-[[1-[2-(2H-tetrazol-5-yl)-phenyl]-1H-indol-4-yl]methyl]-1H-imidazole-5-carboxylic acid, 2-methyl-1-(2-methyl-1-oxopropoxy)propyl ester, monopotassium salt

A.

2-Chloro-3-methylbutanoic acid, 1-methylethyl ester

To freshly fused zinc chloride (27.3 mg) and isobutyrylchloride(4.92 ml, 46.9 mmol) in methylene chloride (10 ml) at 10° C. was added isobutyraldehyde (freshly distilled) (4.26 ml, 46.9 mmol) dropwise, maintaining the temperature at <25° C. Once the addition was complete, the reaction was stirred for 2.5 hours at room temperature. The reaction mixture was then washed with 20% NaOAc, dried over anhydrous magnesium sulfate, filtered and concentrated in vacuo to give the title A compound (6.0 g) as a clear liquid.

B.

2-Butyl-4-chloro-1-[[1-(2-cyanophenyl)-1H-indol-4-yl]methyl]-1H-imidazole-5-carboxylic acid, 2-metyl-1-(2-methyl-1-oxopropoxy)propyl ester 2-Butyl-4-chloro-1-[[1-(2-cyanophenyl)-1H-indol-4-yl]methyl]-1H-imidazole-5-carboxylic acid (630 mg, 1.46 mmol, prepared as described in part C of Example 9), the title A compound (1.04 g, 5.84 mmol), sodium iodide (438 mg, 2.92 mmol) cesium carbonate (2.14 g, 6.57 mmol) and dimethylformamide (3.2 mL) were combined and stirred at 60° C. for 7 hours. The reaction mixture was diluted with ethyl acetate and filtered. The organic phase was washed with pH 4 buffer (2×25 ml), pH 7 buffer (2×25 ml), saturated sodium chloride (1×25 ml), dried over anhydrous magnesium sulfate, filtered and concentrated to give a clear oil. Purification by chromatography on Merck silica gel (240 ml) eluting with 2:7 ethyl acetate:hexane gave the title B compound (451 mg).

C.

2-Butyl-4-chloro-1-[[1-[2-(2H-tetrazol-5-yl)phenyl]-1H-indol-4-yl]methyl]-1H-imidazole-5-carboxylic acid, 2-methyl-1-(2-methyl-1-oxopropoxy)propyl ester The title B compound (451 mg, 0.784 mmol) and tributyltin azide (1.3 g, 3.9 mmol) in xylenes (0.45 ml) was stirred in a stoppered flask at 93° C. for 17.5 hours. The reaction mixture was placed directly on Merck silica (46 g) for chromatography, eluting with ethyl acetate:hexane:acetic acid (40:59:1). Product containing fractions were collected and were repurified on Merck silica gel eluting with ethyl acetate:acetic acid:hexane (35:1:64). The title C compound (435 mg) was obtained as an oil.

D.

2-Butyl-4-chloro-1-[[1-[2-(2H-tetrazol-5-yl)phenyl]-1H-indol-4-yl]methyl]-1H-imidazole-5-carboxylic acid, 2-methyl-1-(2-methyl-1-oxopropoxy)propyl ester, monopotassium salt To the title C compound (424 mg, 0.70 mmol) in acetone (1 ml) was added 1M potassium hydrogen carbonate (0.75 ml, 0.75 mmol) to pH=8. TLC indicated some decomposition at this point. The solution was concentrated in vacuo and purified by HP-20. The product, eluting in 25%–30% acetone/water was filtered and lyophilized with ~30 ml ethanol to give the title compound as a white lyophillate (280 mg).

EXAMPLE 14

2-Butyl-4-chloro-1-[[1-[2-(2H-tetrazol-5-yl)phenyl]-1H-indol-4-yl]methyl]-1H-imidazole-5-carboxylic acid, 1-(2,2-dimethyl-1-oxopropoxy)-2-methylpropyl ester, monopotassium salt

A.

2,2-Dimethylpropanoic acid, 1-chloro-2-methylpropyl ester

To freshly fused zinc chloride (27.3 mg) and trimethylacetylchloride (5.11 ml, 41.5 mmol) in methylene chloride(10 ml) at 10° C. was added isobutyraldehyde (freshly distilled) (3.77 ml, 41.5 mmol) dropwise, maintaining the temperature at <25° C. Once the addition was complete, the reaction was stirred for one hour at room temperature. The reaction mixture was then washed with 20% NaOAc, dried over anhydrous magnesium sulfate, filtered and concentrated in vacuo to give the title A compound (3.25 g) as a clear liquid.

B.

2-Butyl-4-chloro-1-[[1-(2-cyanophenyl)-1H-indol-4-yl]methyl]-1H-imidazole-5-carboxylic acid, 2-methyl-1-(2,2-dimethyl-1-oxopropoxy)propyl ester A mixture containing 2-butyl-4-chloro-1-[[1-(2-cyanophenyl)-1H-indol-4-yl]methyl]-1H-imidazole-5-carboxylic acid (550 mg, 1.27 mmol, prepared as described in part C of Example 9), the title A compound (979 mg, 5.08 mmol), sodium iodide (381 mg, 2.54 mmol) and cesium carbonate (1.86 g, 5.72 mmol) in 2.5 mL of dimethylformamide was heated at 60° C. for 7 hours in a stoppered flask. Upon cooling the reaction mixture was diluted with 110 mL of ethyl acetate and filtered. The organic extract was rinsed with three 15 mL portions of pH 4 buffer, 20 mL of 1:1, water:brine and 30 mL of brine, then dried over anhydrous magnesium sulfate and concentrated in vacuo to afford 1.3 g of crude product. Chromatography on 75 g of silica gel eluted with 4:1, hexanes:ethyl acetate yielded 567 mg of the title B compound.

C.

2-Butyl-4-chloro-1-[[1-[2-(2H-tetrazol-5-yl)phenyl]-1H-indol-4-yl]methyl]-1H-imidazole-5-carboxylic acid, 1-(2,2-dimethyl-1-oxopropoxy)-2-methylpropyl ester, monopotassium salt The title B compound (553 mg, 0.939 mmol), tributyltin azide (1.56 g, 4.69 mmol) and xylenes (1 mL) were combined and heated in a stoppered flask at 93° C. for 18 hours. The reaction mixture was then cooled and directly chromatographed on 100 g of silica gel eluted with 40:1:80, ethyl acetate:acetic acid:hexanes. Product containing fractions were pooled, concentrated in vacuo and evaporated with toluene to yield 533 mg of the parent acid form of the title compound (0.843 mmol). The acid was converted to the corresponding potassium salt by addition of potassium hydrogen carbonate (101 mg, 1.01 mmol) and water to the parent acid dissolved in minimal methanol. Purification by reverse phase HP-20 chromatography using water-acetone elution yielded the title compound (0.49 g).

EXAMPLE 15

2-Butyl-4-chloro-1-[[1-[2-(2H-tetrazol-5-yl)-phenyl]-1H-indol-4-yl)methyl]-1H-imidazole-5carboxylic acid, 2-(diethylamino)-2-oxoethyl ester, monopotassium salt

A.

2-Chloro-N,N-diethylacetamide

To a solution of chloroacetic acid (10 g, 0.11 mol) in methylene chloride (530 ml) at 0° C. was added diethylamine HCl (15.3 g, 0.14 mol), 1-(3-dimethylaminopropyl)-3-ethyl carbodiimide hydrochloride (26.4 g, 0.14 mol) and 4-methyl morpholine (29 ml, 0.27 mol). After the reaction stirred 1 hour at 0° C., the reaction was stirred at room temperature for 4 hours. The reaction mixture was then washed with water, 1N hydrochloric acid (until the aqueous phase was colorless) and saturated sodium chloride, dried over anhydrous magnesium sulfate, filtered and concentrated to give the title A compound as a yellow oil (9.3 g).

B.

2-Butyl-4-chloro-1-[[1-(2-cyanophenyl)-1H-indol-4-yl]methyl]-1H-imidazole-5-carboxylic acid, 2-(diethylamino)-2-oxoethyl ester 2-Butyl-4-chloro-1-[[1-(2-cyanophenyl)-1H-indol-4-yl]methyl]-1H-imidazole-5-carboxylic acid (331 mg, 0.77 mmol, prepared as described in part C of Example 9), the title A compound (229 mg, 1.53 mmol), sodium iodide (172 mg, 1.15 mmol) cesium carbonate (622 mg, 1.91mmol) and dimethylformamide (1.5 mL) were combined and stirred at room temperature for 5.5 hours. The reaction mixture was diluted with ethyl acetate and filtered. The organic phase was washed with pH 4 buffer (3×30 ml), pH 7 buffer (3×30 ml), saturated sodium chloride (1×30 ml), dried over anhydrous magnesium sulfate, filtered and concentrated to give a yellow oil. Purification by chromatography using Merck silica gel (250 ml) eluting with 40% ethyl acetate/hexane gave 401 mg of the title B compound.

C.

2-Butyl-4-chloro-1-[[1-[2-(2H-tetrazol-5-yl)phenyl]-1H-indol-4-yl]methyl]-1H-imidazole-5-carboxylic acid, 2-(diethylamino)-2-oxoethyl ester The title B compound (401 mg, 0.79 mmol) and tributyltin azide (0.8 g, 2.4 mmol) in xylenes (0.8 ml) were stirred in a stoppered flask at 100° C. for 24 hours. The reaction mixture was placed directly on Merck silica gel (46 g) for chromatography eluting with ethyl acetate:-hexane: acetic acid (70:29:1). Two fractions were collected which were repurified separately on Merck silica gel eluting each with ethyl acetate: acetic acid:hexane (60:1:39). The title C compound (484 mg)was obtained as a yellow solid.

D.

2-Butyl-4-chloro-1-[[1-[2-(2H-tetrazol-5-yl)phenyl]-1H-indol-4-yl)methyl]-1H-imidazole-5-carboxylic acid, 2-(diethylamino)-2-oxoethyl ester, monopotassium salt To the title C compound (484 mg, 0.82 mmol) in methanol (1 ml) was added 1M potassium hydrogen carbonate (0.9 ml, 1.1 mmol) to pH=8. The solution was concentrated in vacuo and purified by HP-20 reverse phase chromatography. The product fractions, eluted with 20–30% ethanol/water, were filtered and lyophilized to give the title compound as a light yellow lyophillate (270 mg).

EXAMPLE 16

2-Butyl-1-[[1-[2-(2H-tetrazol-5-yl)phenyl]-1H-indol-4-yl]-methyl]-1H-imidazole-5-carboxylic acid

A.

2-Butyl-1-[[2,3-dibromo-1-(2-cyanophenyl)-1H-indol-4-yl]methyl]-1H-imidazole-5-carboxaldehyde To 2-butyl-1H-imidazole-5-carboxaldehyde (161 mg, 1.058 mmol, 1 eq., prepared as described in part H of Example 1) and 2-[2,3-dibromo-4-(bromomethyl)-1H-indol-1-yl]benzonitrile (546 mg, 1.164 mmol, 1.1 eq., prepared as described in part C of Example 9) in dimethylformamide (4.4 ml, 0.24M), cesium carbonate (862 mg, 2.646 mmol, 2.5 eq.) was added. The mixture was stirred at 50° C. for 2 hours. Methylene chloride was added and the mixture was filtered. The filtrate was washed with water, dried over anhydrous magnesium sulfate and concentrated. The residue was chromatographed on silica gel eluting with toluene: ethyl ether (4:1) to give the title A compound (451 mg). TLC: $R_f = 0.4$, silica gel, Hexane:ethyl acetate (2:3).

B.

2-Butyl-1-[[1-(2-cyanophenyl)-1H-indol-4-yl]methyl]-1H-imidazole-5-carboxylic acid To the title A compound (451 mg, 0.835 mmol, 1 eq.) and sulfamic acid (284 mg, 2.922 mmol, 3.5 eq.) in tetrahydrofuran (8.4 ml, 0.1M) at 0° C., a solution of sodium chlorite (264 mg, 2.922 mmol, 3.5 eq.) in water (8.4 ml, 0.1M) was added. The reaction was stirred at 0° C. for 30 minutes. Water (15 ml) was added. The mixture was extracted with 10% methanol in methylene chloride. The extract was dried over anhydrous magnesium sulfate and concentrated to give 2-butyl-1-[[2,3-dibromo-1-(2-cyanophenyl)-1H-indol-4-yl]methyl]-1H-imidazole-5-carboxylic acid.

To 2-butyl-1-[[2,3-dibromo-1-(2-cyanophenyl)-1H-indol-4-yl]methyl]-1H-imidazole-5carboxylic acid in ethanol (26 ml, 0.032M), sodium hydroxide water solution (1N, 2.923 ml, 2,923 mmol, 3.5 eq.), and palladium hydroxide on carbon (186 mg) were added. The mixture was placed under a balloon of hydrogen gas and stirred at room temperature. After 1.5 hours, 20 ml water and 40 ml methanol were added and the reaction was filtered. The filtrate was concentrated to about 20 ml and acidified with 1N HCl to pH~2. The mixture was extracted with 10% methanol in methylene chloride. The extract was washed with brine and concentrated. The residue was chromatographed on silica gel eluting with EtOAc: Pyridine:AcOH:H2O (40:1:1:0.5) to give the title B compound (200 mg).

C.

2-Butyl-1-[[1-[2-(2H-tetrazol-5-yl)phenyl]-1H-indol-4-yl]-methyl]-1H-imidazole-5-carboxylic acid A mixture of the title B compound (184 mg, 0.462 mmol, 1 eq.), tributyltin azide (613 mg, 1.847 mmol, 4 eq.) and xylene (4.6 ml, 0.1M) was stirred at 120° C. for 24 hours. After cooling, the mixture was concentrated and the residue was chromatographed on silica gel eluting with ethyl acetate:acetic acid (100:1) and then ethyl acetate: pyridine:acetic acid:water (100:10:10:5) to give a solid which was purified again by HPLC on a YMC 5-10 ODS column eluting with 50% of (H2O:C-H3OH:CF3CO2H, 90:10:0.1) and 50% of (H2O:C-H3OH:CF3CO2H, 90:800:0.9) to give the title compound (140 mg).

EXAMPLE 17

2-Butyl-4-chloro-1-[[1-[2-(2H-tetrazol-5-yl)-phenyl]-1H-indole-4-yl]methyl]-1H-imidazole-5-carboxylic acid, 1-(acetyloxy) ethyl ester, monopotassium salt

A.

1-Chloroethyl acetate

To freshly fused zinc chloride (0.25 g) and acetyl chloride (11 ml, 150.0 mmol) at 10° C. was added acetaldehyde (8.4 ml, 150 mmol) dropwise, maintaining the temperature at <20° C. Once the addition was complete, the reaction was stirred for two hours at room temperature. The reaction was partitioned between methylene chloride and NaOAc and the organic phase was washed twice with 20% NaOAc before being concentrated in vacuo to a brown liquid. Purification by distillation at 28 mm of Hg, 37°–39° C. gave the title A compound (4.2 g) as a clear liquid.

B.

2-Butyl-4-chloro-1-[[1-(2-cyanophenyl)-1H-indol-4-yl]methyl]-1H-imidazole-5-carboxylic acid, 1-(acetyloxy)ethyl ester 2-Butyl-4-chloro-1-[[1-(2-cyanophenyl)-1H-indol-4-yl]methyl]-1H-imidazole-5-carboxylic acid (910 mg, 2.1 mmol, prepared as described in part C of Example 9), the title B compound (930 mg, 7.6 mmol), sodium iodide (795 mg, 5.03 mmol), cesium carbonate (2.6 g, 7.98 mmol) and dimethylformamide (4.0 mL) were combined and were stirred at room temperature for 16 hours. The reaction was diluted with ethyl acetate and filtered. The organic phase was washed with pH=4 buffer twice, pH 7 buffer once, saturated sodium chloride once, dried over anhydrous magnesium sulfate, filtered and concentrated to give a yellow oil. Purification by chromatography on Merck silica gel (250 g) eluting with (8:2) hexane/ethyl acetate gave the title B compound (1.06 g).

C.

2-Butyl-4-chloro-1-[[1-[2-(2H-tetrazol-5-yl)phenyl]-1H-indol-4-yl]methyl]-1H-imidazole-5-carboxylic acid, 1-(acetyloxy)ethyl ester The title B compound (943 mg, 1.82 mmol), tributyltin azide (2.41 g, 7.27 mmol) and xylenes (0.9 mL) were heated at 65° C. for 42 hours. More tributyltin azide (0.7 g, 2.11 mmol) was added and the reaction was heated for 4 more hours at 70° C. The crude reaction mixture was diluted with 1 mL of methylene chloride and flash chromatographed on 130 g of Merck silica gel eluted with 35:1:65, ethyl acetate:acetic acid:hexanes followed by 50:5:50, ethyl acetate:acetic acid:hexanes to yield the title C compound.

D.

2-Butyl-4-chloro-1-[[1-[2-(2H-tetrazol-5-yl)phenyl]-1H-indole-4-yl]methyl]-1H-imidazole-5-carboxylic acid, 1-(acetyloxy) ethyl ester, monopotassium salt To the title C compound (783 mg, 1.32 mmol) in absolute ethanol (1 ml) was added 1M potassium hydrogen carbonate (1.45 mmol, 1.1 ml) to pH 8. The solution was concentrated in vacuo and purified twice by HP-20 reverse phase chromatography. The product fractions, eluted in 25–40% ethanol/water, were pooled, filtered and lyophilized to give the title compound as a white solid (534 mg).

EXAMPLE 18

2-Butyl-4-chloro-1-[[1-[2-(2H-tetrazol-5-yl)-phenyl]-1H-indol-4-yl]methyl]-1H-imidazole-5carboxylic acid, 2,3-dihydro-1H-inden-5-yl ester

A.

2-Butyl-4-chloro-1-[[1-(2-cyanophenyl)-1H-indol-4-yl]methyl]-1H-imidazole-5-carboxylic acid, 5-indanyl ester To a mixture containing 2-butyl-4-chloro-1-[[1-(2-cyanophenyl)-1H-indol-4-yl]methyl]-1H-imidazole-5-carboxylic acid (903 mg, 2.03 mmol, prepared as described in part C of Example 9), 5-indanol (307 mg, 2.29mmol), 2,6-dimethylaminopyridine (50.8 mg, 0.416 mmol) and triethylamine (0.377 mL, 2.70 mmol) in 9 mL of dichloromethane cooled in an ice bath was added 1-(3-dimethylaminopropyl)-3-ethylcarbodiimide hydrochloride (519 mg, 2.70 mmol). The stoppered reaction mixture was allowed to warm to ambient temperature overnight, then diluted with methylene chloride and rinsed with water and saturated aqueous sodium chloride solution. The organic extract was dried over anhydrous magnesium sulfate and concentrated in vacuo to give 1.83 g of crude product. Flash chromatography on 75 g of silica gel eluted with 8:2, hexanes:ethyl acetate gave 1.03 g of the title A compound.

B.

2-Butyl-4-chloro-1-[[1-[2-(2H-tetrazol-5-yl)phenyl]-1H-indol-4-yl]methyl]-1H-imidazole-5-carboxylic acid, 2,3-dihydro-1H-inden-5-yl ester A mixture of the title A compound (1.03 g, 1.88 mmol), tributyltin azide (1.87 g, 5.63 mmol) and xylenes (2 mL) was heated in a stoppered flask at 88° C. for 19 hours, then an additional 0.7 g of tributyltin azide was added and heating continued for 6 hours. The reaction mixture was then cooled and directly chromatographed on 200 g of silica gel eluted with 35:1:65, ethyl acetate:acetic acid:hexanes. Product containing fractions were pooled, concentrated in vacuo and evaporated with toluene to yield 940 mg of the title compound.

EXAMPLE 19

2-Butyl-4-chloro-1-[[1-[2-(2H-tetrazol-5-yl)-phenyl]-1H-indole-4-yl]methyl]-1H-imidazole-5-carboxylic acid, 2-methyl-1-(1-oxopropoxy)propyl ester, monopotassium salt

A.

1-Chloro-2-methylpropyl propanoate

To freshly fused zinc chloride (41 mg) in methylene chloride (10 ml) was added propionyl chloride (5.0 g, 54.0mmol). The reaction was cooled to 10° C. and isobutyraldehyde (3.89 g, 54.0 mmol) was added dropwise maintaining the temperature at 25° C. Once the addition was complete, the reaction Was Stirred for one hour at room temperature. The reaction mixture was washed with 20% NaOAc and the organic phase was concentrated in vacuo to provide the title A compound.

B.

2-Butyl-4-chloro-1-[[1-(2-cyanophenyl)-1H-indol-4-yl]methyl]-1H-imidazole-5-carboxylic acid, 2-methyl-1-(1-oxopropoxy)propyl ester 2-Butyl-4-chloro-1-[[1-(2-cyanophenyl)-1H-indol-4-yl]methyl]-1H-imidazole-5-carboxylic acid (870 mg, 2.01 mmol, prepared as described in part C of Example 9), the title A compound (1.16 g, 7.03 mmol), sodium iodide (754 mg, 5.03 mmol), cesium carbonate (2.3 g, 7.03 mmol) and dimethylformamide (4.4 mL) were combined and heated to 80° C. for 6 hours. The reaction mixture was diluted with ethyl acetate, filtered and washed with pH 4 buffer, water and brine, dried over anhydrous magnesium sulfate and concentrated in vacuo to 1.50 g of crude product. Flash chromatography on 70 g of Merck silica gel eluted with 8:2, hexanes::ethyl acetate yielded the title B compound (0.84 g).

C.

2-Butyl-4-chloro-1-[[1-[2-(2H-tetrazol-5-yl)phenyl]-1H-indol-4-yl]methyl]-1H-imidazole-5-carboxylic acid, 2-methyl-1-(1-oxopropoxy)propyl ester The title B compound (840 mg, 1.50 mmol), tributyltin azide (1.99 g, 6 mmol) and xylenes (2 mL) were heated at 80° C. for 27 hours in a stoppered flask. The reaction mixture was cooled to room temperature and directly chromatographed on 144 g of Merck silica gel eluted with 35:1:65, ethyl acetate acetic acid:hexanes. Pooling of product containing fractions afforded 682 mg of the title C compound.

D.

2-Butyl-4-chloro-1-[[1-[2-(2H-tetrazol-5-yl)phenyl]-1H-indole-4-yl]methyl]-1H-imidazole-5-carboxylic acid, 2-methyl-1-(1-oxopropoxy)propyl ester, monopotassium salt To the title C compound (682 mg, 1.06 mmol) in absolute ethanol (1 ml) was added 1M potassium hydrogen carbonate (1.11 ml, 1.11 mmol) to pH=8. The solution was concentrated in vacuo and purified by HP-20 reverse phase chromatography. The product fractions, eluted in 35–40% ethanol/water, were combined, filtered and lyophilized to give the title compound as a white solid (517 mg).

EXAMPLE 20

2-Butyl-4-chloro-1-[[1-[2-(2H-tetrazol-5-yl)-phenyl]-1H-indole-4-yl]methyl]-1H-imidazole-5-carboxylic acid, ethyl ester, monopotassium salt

A.

2-Butyl-4-chloro-1-[[1-(2-cyanophenyl)-1H-indol-4-yl]methyl]-1H-imidazole-5-carboxylic acid, ethyl ester Ethyl iodide (561.5 mg, 3.60 mmol) and cesium carbonate (1.5g, 4.5 mmol) were added to a solution of 2-butyl-4-chloro-1-[[1-(2-cyanophenyl)-1H-indol-4-yl]methyl]-1H-imidazole-5carboxylic acid (779.2 mg, 1.80 mmol, prepared as described in part C of Example 9) in dimethylformamide (3.72 ml). After 1.5 hours at room temperature, the reaction was diluted with ethyl acetate and filtered to remove the cesium carbonate. The ethyl acetate was washed with pH=4 buffer (2×20 ml), pH=7 buffer (2×25 ml), saturated sodium chloride (20 mL) and dried over anhydrous magnesium sulfate, filtered and concentrated to a yellow oil (890 mg). Purification by flash chromatography (83 g Merck silica gel, 8:2 hexane/ethyl acetate) gave 662 mg of the title A compound.

B.

2-Butyl-4-chloro-1-[[1-[2-(2H-tetrazol-5-yl)phenyl]-1H-indol-4-yl]methyl]-1H-imidazole-5-carboxylic acid, ethyl ester The title A compound (598.8 mg, 1.3 mmol) and tributyltin azide (1.73 g, 5.2 mmol) in xylenes (6.64 ml) was stirred capped at 100° C. for 30 hours. More tributyltin azide (0.65 g, 1.95 mmol) was added and heating continued for 18 hours. The reaction mixture was placed directly on Merck silica (228 ml) for purification, eluting with ethyl acetate:hexane:acetic acid (35:64:1). The title B compound (585.3 mg) was obtained as a yellow solid.

C.

2-Butyl-4-chloro-1-[[1-[2-(2H-tetrazol-5-yl)phenyl]-1H-indol-4-yl]methyl]-1H-imidazole-5-carboxylic acid, ethyl ester, monopotassium salt To the title B compound (584 mg, 1.19 mmol) in absolute ethanol (1 ml) was added 1M potassium hydrogen carbonate (1.31 ml, 1.31 mmol) to pH=8. The solution was concentrated in vacuo and purified by HP-20. The product, eluted in 25–40% ethanol/water was filtered and lyophilized to give the title compound as a white solid (510 mg).

EXAMPLE 21

2-Butyl-1-[[1-[2-(2H-tetrazol-5-yl)phenyl]-1H-indol-4-yl]methyl]-4-(trifluoromethyl)-1H-imidazole-5-carboxylic acid, ethyl ester

A.

4,4,4-Trifluoro-2-(hydroxyimino)-3-oxobutanoic acid, ethyl ester

A solution of sodium nitrite (0.29 mmol) in 35 mL of water was added dropwise over 50 minutes to a stirred, ice-cooled solution of 22.8 g of ethyl 4,4,4-trifluoroacetoacetate (0.12 mmol) in 30 mL of acetic acid. The reaction was continued for 2 hours, with gradual warming to 15° C. Water and acetic acid were removed under reduced pressure (azeotroped with toluene). The crude product was partitioned between ethyl acetate and saturated aqueous potassium hydrogen carbonate solution. The layers were separated. The ethyl acetate layer was washed with saturated aqueous potassium hydrogen carbonate solution and brine, dried over sodium sulfate and concentrated to yield 21.4 g of the title A compound as a light yellow oil.

B.

2-Butyl-1-hydroxy-4-(trifluoromethyl)-1H-imidazole-5-carboxylic acid, ethyl ester A solution of valeraldehyde (9.87 mL, 92.9 mmol) in 150 mL of saturated ethanolic ammonia was cooled to 0° C. and added to the title A compound (19.8 g, 92.9 mmol). The red-orange solution was stirred at 0° C. under an argon atmosphere for 30 minutes and subsequently at room temperature overnight. The solvent was removed under reduced pressure and co-evaporated with ether. The residue was dissolved in 150 mL of ether and 0.1 g of insoluble material was removed by filtration. Concentration of the filtrate under reduced pressure yielded 27.7 g of a light yellow-orange taffy. Flash chromatography on 750 g of silica gel eluting with 2L of methylene chloride followed by 98:1:1 methylene chloride:methanol:acetic acid yield the title B compound (9.8 g) as a light yellow solid, m.p. 77.5°–80.5° C.

C.

2-Butyl-4-(trifluoromethyl)-1H-imidazole-5-carboxylic acid, ethyl ester

To a mixture of the title B compound (4.25 g, 15.00 mmol) and sodium acetate (15 g) in methanol (50 mL) and water (50 mL) at an ice bath temperature, titanous chloride solution (50 mL of 20% solution) was added dropwise over 20 minutes with stirring. After an hour at 0° C., the reaction mixture was warmed to room temperature and stirred for one hour. The reaction product was extracted with ethyl acetate (2×300 mL). The combined organic layer was washed with citric acid (100 mL of 5% solution) followed by aqueous sodium bicarbonate solution (100 mL), dried over anhydrous magnesium sulfate and concentrated in vacuo to obtain the title C compound (3.42 g) as a solid, m.p. 51.0°–53.0° C.

D.

1H-Imidazole-4-carboxylic acid, methyl ester

To a solution of 2-butyl-1-hydroxy-4-(trifluoromethyl)-1H-imidazole-5-carboxylic acid, ethyl ester (506 mg, 3.14 mmol) dissolved in a mixture of 5 mL of methanol and 10 mL of diethyl ether was added ethereal diazomethane until disappearance of starting acid was indicated by TLC. Anhydrous magnesium sulfate was then added and the solution filtered and concentrated in vacuo. Flash chromatography on 10 g of Merck silica gel eluted with 2:1, CHCl$_3$:hexanes, followed by 10:1, CHCl$_3$:Et$_2$O afforded the title D compound (540 mg).

E.

1-(2-Cyanophenyl)-1H-indole-4-carboxylic acid, methyl ester

A mixture of the title D compound (40.6 mg, 0.232 mmol), 2-fluorobenzonitrile (38 μL, 0.348 mmol), potassium carbonate (64.1 mg, 0.464 mmol) and 18-crown-6 (6.1 mg, 0.0232 mmol) in 0.23 mL of dimethylformamide was heated at 150° C. for 150 minutes. Upon cooling to room temperature, the reaction mixture was diluted with ethyl acetate, filtered and rinsed with pH 4 buffer. The aqueous layer was further extracted with two more portions of ethyl acetate and the combined organic extract was rinsed with brine, dried over sodium sulfate, filtered over anhydrous magnesium sulfate and concentrated in vacuo. Flash chromatography on 5 g of Merck silica gel eluted with 5:1, CHCl$_3$:hexanes, followed by 100% CHCl$_3$ afforded the title E compound (61.6 mg).

F.

1-(2-Cyanophenyl)-1H-indole-4-carboxylic acid

The title E compound (8.0 g, 28.95 mmol), 1N sodium hydroxide (43.4 ml, 43.4 mmole), methanol (43.4 ml, 43.4 mmole) and tetrahydrofuran (43.4 ml) were combined and heated at 50° C. After 4 hours 40 minutes, the reaction was cooled to room temperature and 10% hydrochloric acid (~50 ml) was added to precipitate a white solid. The mixture was filtered and the product was collected as a white solid (7.2 g).

G.

2-[4-(Hydroxymethyl)-1H-indol-1-yl]benzonitrile

Borane-tetrahydrofuran complex (1M in tetrahydrofuran, 27.3 ml) was added to a solution of the title F compound (7.17 g, 27.3 mmole) in tetrahydrofuran (distilled, 27.3 ml) at −20° C., warmed to room temperature and stirred for 21 hours. The solution was cooled to 0° C. and quenched with 1N sodium hydroxide to pH=14. The solution was extracted with ether (3×100 ml), washed with sodium chloride, dried over anhydrous magnesium sulfate, filtered and concentrated to a light green solid. The solid was recrystallized twice from ethyl acetate/hexane to yield the title G compound (5.54 g).

H.

2-[4-(Bromomethyl)-1H-indol-1-yl]benzonitrile

To a solution of the title G compound (5.46 g, 22 mmole) in methylene chloride (distilled, 60 ml) at 0° C. was added CBr$_4$ (10.2 g, 30.8 mmole) and triphenylphosphine (7.5 g, 28.6 mmole). The reaction was stirred for 15 minutes at 0° C. and was then warmed to room temperature. After 2.5 hours, the reaction was diluted in methylene chloride and placed directly on a Merck silica gel column (66 g) eluting with (1:1) toluene/hexane for purification. The product fractions were collected and concentrated then triturated with cold ethyl acetate to obtain the title H compound (5.8 g).

I.

2-Butyl-1-[[1-(2-cyanophenyl)-1H-indol-4-yl]methyl]-4-(trifluoromethyl)-1H-imidazole-5-carboxylic acid, ethyl ester A mixture of the title C compound (470 mg, 1.78 mmol) and cesium carbonate (585 mg, 1.8 mmol) in dimethylformamide (4 mL) was stirred at room temperature for 15 minutes. To this reaction mixture was added the title H compound (555 mg, 1.78 mmol). The resulting mixture was stirred at room temperature for 3 hours. The solid was filtered and washed with ethyl acetate. The filtrate solution was concentrated in vacuo and the residue was purified by flash column chromatography (SiO$_2$, ethyl acetate:hexane 1:2) to obtain the title I compound (870 mg) as an oil.

J.

2-Butyl-1-[[1-[2-(2H-tetrazol-5-yl)phenyl]-1H-indol-4-yl]methyl]-4-(trifluoromethyl)-1H-imidazole-5-carboxylic acid, ethyl ester A solution of the title I compound (800 mg, 1.62 mmol) and tri-n-butyltin azide (1.88 g, 5.66 mmol) in xylene (5 mL) was stirred at 100°–110° C. for 24 hours. The reaction mixture was concentrated in vacuo and the residue was purified by preparative chromatography. The fractions containing the desired product were combined and concentrated to obtain the title compound (675 mg), m.p. 93.0°–95.0° C.

EXAMPLE 22

2-Butyl-1-[[1-[2-(2H-tetrazol-5-yl)phenyl]-1H-indol-4-yl]methyl]-4-(trifluoromethyl)-1H-imidazole-5-carboxylic acid, disodium salt A mixture of 2-butyl-1-[[1-[2-(2H-tetrazol-5-yl)phenyl]-1H-indol-4-yl]methyl]-4-(trifluoromethyl)-1H-imidazole-5-carboxylic acid, ethyl ester (400 mg, 0.744 mmol) and aqueous sodium hydroxide (2N, 1.5 mL) in methanol (5 mL) was stirred at room temperature overnight. The reaction mixture was concentrated in vacuo and the residue was passed through a column on HP-20 resin eluting with water followed with 30% methanol in water. The fractions containing the desired product were concentrated in vacuo to give the title compound (387 mg), m.p. >250° C.

EXAMPLES 23–82

Using the methodology in the specification and procedures described in the above examples, the following additional compounds are prepared.

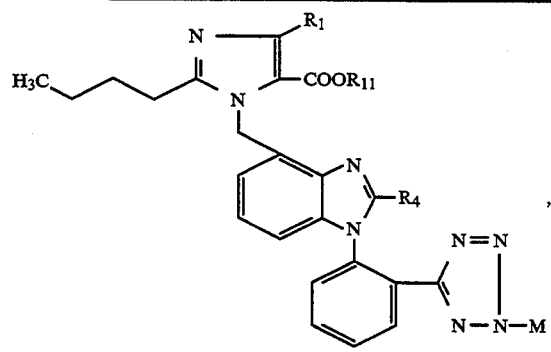

| Ex. | R$_1$ | R$_{11}$ | R$_4$ | M | Solvent | mp °C. | % C | % H | % N | other |
|---|---|---|---|---|---|---|---|---|---|---|
| 23 | Cl | Li | H | Li | 4.82 H$_2$O | >280 | 48.20 | 4.72 | 19.26 | Cl, 5.81 |
| 24 | Cl | Et | H | Li | 1.31 H$_2$O | 202–210 | 56.23 | 5.25 | 20.91 | Cl, 6.57 |
| 25 | Cl | 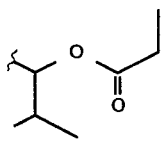 | H | K | | | | | | |

-continued
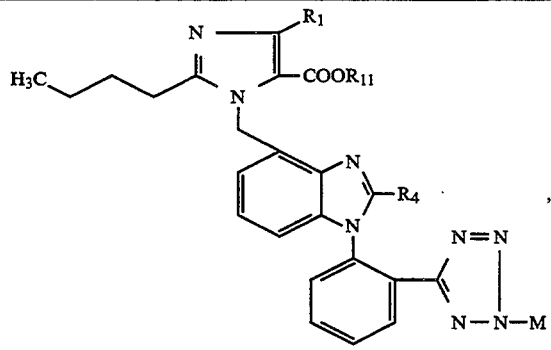
| Ex. | $R_1$ | $R_{11}$ | $R_4$ | M | Solvent | mp °C. | % C | % H | % N | other |
|---|---|---|---|---|---|---|---|---|---|---|
| 26 | Cl | ![iBu isobutyrate] | H | K | | | | | | |
| 27 | $CF_3$ | Na | H | Na | 2.68 $H_2O$ | 245–250 | 48.12 | 4.50 | 18.55 | F, 8.44 |
| 28 | $CF_3$ | Et | H | Li | 2.37 $H_2O$ | 203–210 | 53.28 | 4.98 | 18.98 | F, 9.47 |
| 29 | $CF_3$ | ![iBu propionate] | H | K | | | | | | |
| 30 | $CF_3$ | ![iBu isobutyrate] | H | K | | | | | | |
| 31 | $-CF_2CF_3$ | Li | H | Li | 1.53 $H_2O$ | >220 | 50.37 | 3.40 | 18.37 | F, 15.48 |
| 32 | $-CF_2CF_3$ | Et | H | H | — | oil | 57.47 | 4.64 | 17.36 | F, 15.13 |
| 33 | $-CF_2CF_3$ | ![iBu propionate] | H | H | — | 187–190 | 59.20 | 4.80 | 15.24 | F, 13.57 |
| 34 | $-CF_2CF_3$ | ![iBu isobutyrate] | H | K | | | | | | |
| 35 | Cl | Li | $CF_3$ | Li | 2.5 $H_2O$ | >240 | 47.89 | 4.05 | 18.30 | Cl, 5.77 |
| 36 | Cl | Et | $CF_3$ | K | | | | | | F, 8.61 |
| 37 | Cl | ![iBu propionate] | $CF_3$ | K | | | | | | |
| 38 | Cl | ![iBu isobutyrate] | $CF_3$ | K | | | | | | |
| 39 | $CF_3$ | K | $CF_3$ | K | | | | | | |
| 40 | $CF_3$ | Et | $CF_3$ | K | | | | | | |

-continued
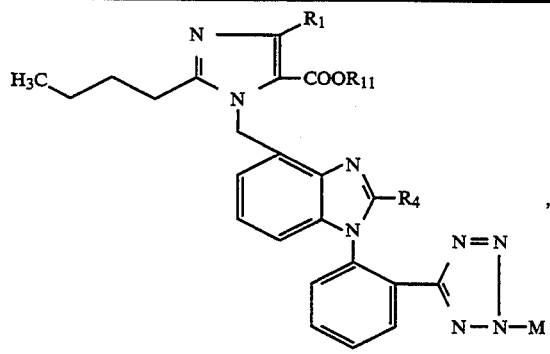
| Ex. | R₁ | R₁₁ | R₄ | M | Solvent | mp °C. | % C | % H | % N | other |
|---|---|---|---|---|---|---|---|---|---|---|
| 41 | CF₃ | ![](o-iPr propanoate) | CF₃ | K | | | | | | |
| 42 | CF₃ | ![](o-iPr isobutanoate) | CF₃ | K | | | | | | |
| 43 | —CF₂CF₃ | K | CF₃ | K | | | | | | |
| 44 | —CF₂CF₃ | Et | CF₃ | K | | | | | | |
| 45 | —CF₂CF₃ | ![](o-iPr propanoate) | CF₃ | K | | | | | | |
| 46 | —CF₂CF₃ | ![](o-iPr isobutanoate) | CF₃ | K | | | | | | |
| 47 | Cl | K | Br | K | | | | | | |
| 48 | Cl | Et | Br | K | | | | | | |
| 49 | Cl | ![](o-iPr propanoate) | Br | K | | | | | | |
| 50 | Cl | ![](o-iPr isobutanoate) | Br | K | | | | | | |
| 51 | CF₃ | K | Br | K | | | | | | |
| 52 | CF₃ | Et | Br | K | | | | | | |
| 53 | CF₃ | ![](o-iPr propanoate) | Br | K | | | | | | |

-continued

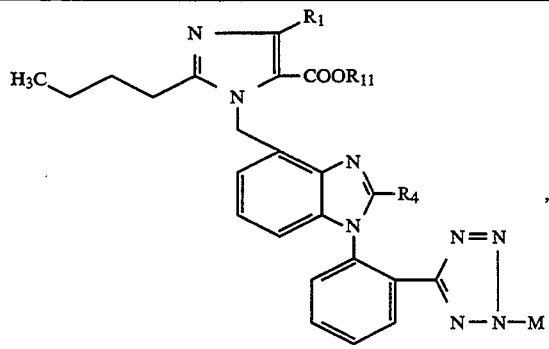

| Ex. | R₁ | R₁₁ | R₄ | M | Solvent | mp °C. | % C | % H | % N | other |
|---|---|---|---|---|---|---|---|---|---|---|
| 54 | CF₃ | ⟨isobutyl isobutyrate group⟩ | Br | K | | | | | | |
| 55 | —CF₂CF₃ | K | Br | K | | | | | | |
| 56 | —CF₂CF₃ | Et | Br | K | | | | | | |
| 57 | —CF₂CF₃ | ⟨isobutyl propanoate group⟩ | Br | K | | | | | | |
| 58 | —CF₂CF₃ | ⟨isobutyl isobutyrate group⟩ | Br | K | | | | | | |
| 59 | Cl | K | Cl | K | | | | | | |
| 60 | Cl | Et | Cl | K | | | | | | |
| 61 | Cl | ⟨isobutyl propanoate group⟩ | Cl | K | | | | | | |
| 62 | Cl | ⟨isobutyl isobutyrate group⟩ | Cl | K | | | | | | |
| 63 | CF₃ | K | Cl | K | | | | | | |
| 64 | CF₃ | Et | Cl | K | | | | | | |
| 65 | CF₃ | ⟨isobutyl propanoate group⟩ | Cl | K | | | | | | |
| 66 | CF₃ | ⟨isobutyl isobutyrate group⟩ | Cl | K | | | | | | |
| 67 | —CF₂CF₃ | K | Cl | K | | | | | | |
| 68 | —CF₂CF₃ | Et | Cl | K | | | | | | |

-continued
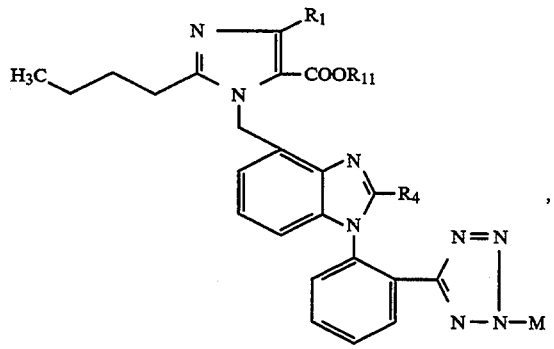
| Ex. | R₁ | R₁₁ | R₄ | M | Solvent | mp °C. | % C | % H | % N | other |
|---|---|---|---|---|---|---|---|---|---|---|
| 69 | —CF₂CF₃ | (sec-butyl propanoate ester) | Cl | K | | | | | | |
| 70 | —CF₂CF₃ | (sec-butyl isobutanoate ester) | Cl | K | | | | | | |
| 71 | Cl | K | F | K | | | | | | |
| 72 | Cl | Et | F | K | | | | | | |
| 73 | Cl | (sec-butyl propanoate ester) | F | K | | | | | | |
| 74 | Cl | (sec-butyl isobutanoate ester) | F | K | | | | | | |
| 75 | CF₃ | K | F | K | | | | | | |
| 76 | CF₃ | Et | F | K | | | | | | |
| 77 | CF₃ | (sec-butyl propanoate ester) | F | K | | | | | | |
| 78 | CF₃ | (sec-butyl isobutanoate ester) | F | K | | | | | | |
| 79 | —CF₂CF₃ | K | F | K | | | | | | |
| 80 | —CF₂CF₃ | Et | F | K | | | | | | |
| 81 | —CF₂CF₃ | (sec-butyl propanoate ester) | F | K | | | | | | |

-continued

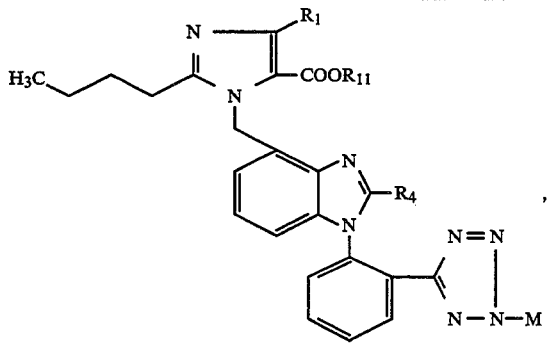

| Ex. | R₁ | R₁₁ | R₄ | M | Solvent | mp °C. | % C | % H | % N | other |
|---|---|---|---|---|---|---|---|---|---|---|
| 82 | —CF₂CF₃ | 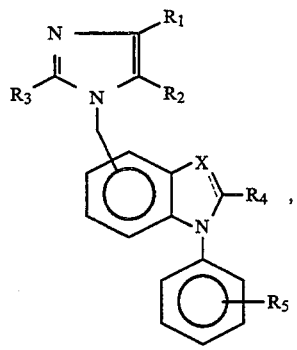 | | F | K | | | | | |

What is claimed is:

1. A compound of the formula

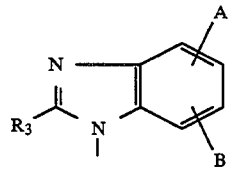

I or pharmaceutically acceptable salts or prodrugs thereof;

where X is —N—;
when X=N, the double bond is always present;
$R_1$ is hydrogen, halogen, —$NO_2$, haloalkyl or —CN;
$R_2$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; —$(CH_2)_m$-imidazol-1-yl; —$(CH_2)_m$-1,2,3-triazolyl optionally substituted with one or two groups selected from $CO_2R_7$ or alkyl of 1 to 4 carbon atoms; —$(CH_2)_m$-tetrazolyl; —$(CH_2)_nOR_6$;

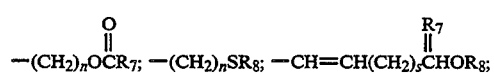

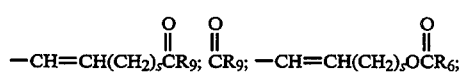

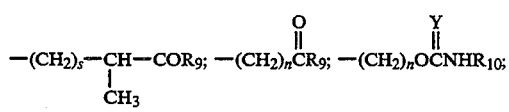

—$(CH_2)_nNR_6COR_{10}$;  —$(CH_2)_nNR_6CNHR_{10}$;

—$(CH_2)_nNR_6SO_2R_{10}$;  —$(CH_2)_nNR_6CR_{10}$;  —$(CH_2)_mF$;

—$(CH_2)_mONO_2$;  —$(CH_2)_mN_3$;  —$(CH_2)_mNO_2$;

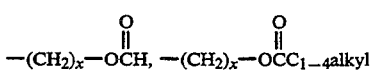

or $R_1$ and $R_2$ taken together with the carbon atoms of the imidazole nucleus to which they are attached form a benzimidazole shown as wherein A is hydrogen, alkyl, $C_xF_{2x+1}$, $C_6F_5$, halogen, $C_{1-6}$alkoxy, —$(CH_2)_xOH$, —$(CH_2)_xOC_{1-4}$alkyl, —$(CH_2)_x$—OCH,  —$(CH_2)_x$—OCC$_{1-4}$alkyl or —$COR_9$ and B is hydrogen, alkyl, $C_xF_{2x+1}$, $C_6F_5$, halogen or $C_{1-6}$alkoxy, with the proviso that when $R_1$ is hydrogen, $R_2$ is other than hydrogen;

$R_3$ is alkyl of 2 to 10 carbon atoms, alkenyl or alkynyl of 3 to 10 carbon atoms or the same groups substituted with F or $CO_2R_7$; cycloalkyl of 3 to 8 carbon atoms; cycloalkylalkyl of 4 to 10 carbon atoms; cycloalkylalkenyl or cycloalkylalkynyl of 5 to 10 carbon atoms; —$(CH_2)_sZ(CH_2)_mR'$ (wherein R' is H, $C_{1-6}$alkyl, $C_{3-6}$cycloalkyl, $C_{2-4}$alkenyl or $C_{2-4}$alkynyl) unsubstituted or substituted by F or $CO_2R_7$; benzyl or benzyl substituted on the phenyl ring with 1 or 2 halogens, alkoxy of 1 to 4 carbon atoms, alkyl of 1 to 4 carbon atoms or nitro;

$R_4$ is hydrogen, halogen, haloalkyl, alkyl, aryl, cycloalkyl, aralkyl, $$-CR_9;\quad \text{(with =O)}$$

$R_5$ is hydrogen, $-CR_9$, $-NHSO_2CF_3$, $-COOCH(R_{15})-OCR_{16}$, $-OS(O)(OH)-OH$, $-SO_3H$, $-C(CF_3)_2OH$, $-O-P(O)(OH)-OH$, $-PO_3H$, $-NHP(O)(OH)-OH$, $-CONHOR_{15}$, $-C(OH)(R_{19})-P(O)(OH)-OH$, tetrazolyl-$R_{11}$, $-CH_2$-tetrazolyl-$R_{11}$, $-CONH$-tetrazolyl-$R_{11}$, $-CONHNHSO_2CF_3$, or triazolyl structures;

$R_6$ is H, alkyl of 1 to 6 carbon atoms, phenyl or benzyl;

$R_7$ is H, alkyl or perfluoroalkyl of 1 to 8 carbon atoms, cycloalkyl of 3 to 6 carbon atoms, phenyl or benzyl;

$R_8$ is H, alkyl of 1 to 6 carbon atoms, cycloalkyl of 3 to 6 carbon atoms, phenyl, benzyl, acyl of 1 to 4 carbon atoms, phenacyl;

$R_9$ is H, alkyl of 1 to 6 carbon atoms, cycloalkyl of 3 to 6 carbon atoms, $(CH_2)_pC_6H_5$, $OR_{11}$ or $NR_{12}R_{13}$;

$R_{10}$ is alkyl of 1 to 6 carbon atoms, or perfluoroalkyl of 1 to 6 carbon atoms, 1-adamantyl, 1-naphthyl, 1-(1-naphthyl)ethyl, or $(CH_2)_pC_6H_5$;

$R_{11}$ is H, alkyl of 1 to 6 carbon atoms, cycloalkyl of 3 to 6 carbon atoms, aryl, arylalkyl, a 5- to 7-membered carbocyclic ring, a 5- to 7-membered carbocyclic ring having another 5- to 7-membered carbocyclic ring fused thereto, $-CH(R_7)-O-C(O)-R_{22}$, dioxolane with $R_{21}, R_{22}$, $-CH_2-C(O)-NR_{21}R_{22}$ or $-CH-C(O)-OR_7$;

or a metal ion, M;

$R_{12}$ and $R_{13}$ independently are H, alkyl of 1 to 4 carbon atoms, phenyl, benzyl, α-methylbenzyl, or taken together form a ring of the formula $$N-(CH_2)_t-Q$$ ;

Q is $NR_{14}$, O or $CH_2$;

$R_{14}$ and $R_{15}$ are independently H, alkyl, aryl, aralkyl or cycloalkyl;

$R_{16}$ is $C_{1-6}$alkyl, $-NR_{17}R_{18}$ or $$-CH(NH_2)-CH_2CO_2R_7;$$

$R_{17}$ and $R_{18}$ are independently H, $C_{1-6}$alkyl, benzyl or taken together are 3 to 6 carbon atoms forming a 4- to 7-membered ring with the nitrogen atom to which they are attached;

$R_{19}$ is H, $C_{1-5}$alkyl, phenyl;

$R_{20}$ is $-CN$, $-NO_2$ or $-CO_2R_7$;

$R_{21}$ is hydrogen, alkyl, cycloalkyl, aryl or arylalkyl and $R_{22}$ is hydrogen, alkyl, cycloalkyl, aryl, arylalkyl or alkoxy or together $R_{21}$ and $R_{22}$ are $-(CH_2)_2-$, $-(CH_2)_3-$, $-CH=CH-$ or ortho-phenylene;

Y=O or S;
Z=O, $NR_6$ or S;
m is 1–5;
n is 1–10;
p is 0–3;
s is 0 to 5;
t is 0 or 1; and
x is 1 to 6.

2. A compound of claim 1 wherein
$R_1$ is hydrogen or halogen;
$R_2$ is $-CH_2OH$, $-CHO$ or $-COOR_{11}$;
$R_3$ is $C_{2-10}$alkyl or $C_{3-10}$alkenyl;
$R_4$ is H or $-COOR_{11}$;
$R_5$ is ortho-tetrazole unsubstituted or substituted by $R_{11}$, or $COOR_{11}$; and
X is $-N$.

3. The compound of claim 1 wherein
$R_1$ is hydrogen, halogen or haloalkyl;
$R_2$ is $-CH_2OH$, $-CHO$ or $-COOR_{11}$;
$R_3$ is $C_{2-10}$alkyl or $C_{3-10}$alkenyl;
$R_4$ is H, halogen or haloalkyl; and
$R_5$ is ortho-tetrazole unsubstituted or substituted by $R_{11}$, or $COOR_{11}$.

4. A compound of claim 1 having the structure

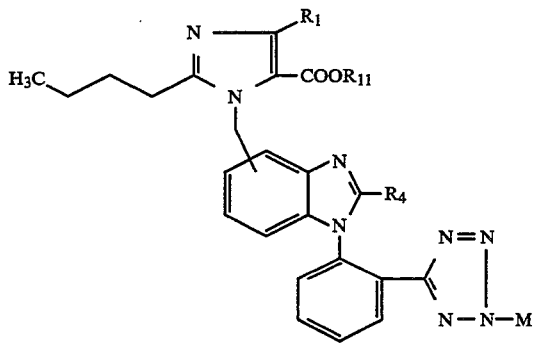

where $R_1$, $R_4$ and $R_{11}$ are as defined in claim 1 and where M is a metal.

5. The compound of claim 4 where
$R_1$ is Cl;
$R_4$ is H;
$R_{11}$ is Li; and,
M is Li.

6. The compound of claim 4 where
$R_1$ is $CF_3$;
$R_4$ is H;
$R_{11}$ is Na; and,
M is Na.

7. The compound of claim 4 where
$R_1$ is $CF_3$;
$R_4$ is H;
$R_{11}$ is ethyl; and,
M is Li.

8. A compound of claim 1 having the name 2-butyl-4-chloro-1-[[1-[2-(2H-tetrazol-5-yl)-phenyl]-1H-benzimidazol-4-yl]methyl]-1H-imidazole-5-methanol, monolithium salt 9. A compound of claim 1 having the name 2-butyl-4-chloro1-[[1-[2-(2H-tetrazol-5-yl)-phenyl]benzimidazol-4-yl]methyl]-1H-imidazole-5-carboxylic acid, dilithium salt.

10. A compound of claim 1 having the name 2-butyl-4-chloro-1-[[1-[2-(2H-tetrazol-5-yl)-phenyl]-1H-benzimidazol-4-yl]methyl]-1H-imidazole-5-carboxylic acid, ethyl ester, monolithium salt.

11. A compound of claim 1 having the name 2-butyl-1-[[1-[2-(2H-tetrazol-5-yl)phenyl]-1H-benzimidazol-4-yl]methyl]-4-(trifluoromethyl)-1H-imidazole-5-carboxylic acid, disodium salt.

12. A compound of claim 1 having the name 2-butyl-1-[[1-[2-(2H-tetrazol-5-yl)phenyl]-1H-benzimidazol-4-yl]methyl]-4-(trifluoromethyl)-1H-imidazole-5-carboxylic acid, ethyl ester, monolithium salt.

13. A compound of claim 1 having the name 2-butyl-4-(1,1,2,2,2-pentafluorethyl)-1-[[1-[2-(2H-tetrazol-5-yl)phenyl]benzimidazol-4-yl]methyl]-1H-imidazole-5-carboxylic acid, dilithium salt.

14. A compound of claim 1 having the name 2-butyl-4-(1,1,2,2,2-pentafluorethyl)-1-[[1-[2-(2H-tetrazol-5-yl)phenyl]benzimidazol-4-yl]methyl]-1H-imidazole-5-carboxylic acid, ethyl ester.

15. A compound of claim 1 having the name 2-butyl-4-(1,1,2,2,2-pentafluorethyl)-1-[[1-[2-(2H-tetrazol-5-yl)phenyl]benzimidazol-4-yl]methyl]-1H-imidazole-5-carboxylic acid, 2-methyl-1-(1-oxopropoxy)propyl ester.

16. A compound of claim 1 having the name 2-butyl-4-chloro-1-[[1-[2-(2H-tetrazol-5-yl)-phenyl]-2-(trifluoromethyl)-1H-benzimidazol-4-yl]methyl]-1H-imidazole-5-carboxylic acid, dilithium salt.

17. A pharmaceutical composition comprising a compound of claim 1 and a pharmaceutically acceptable carrier.

18. A method of treating hypertension comprising administering to a mammalian specie in need thereof a therapeutically effective amount of a composition of claim 17.

19. A method for treating congestive heart failure comprising administering to a mammalian specie in need thereof a therapeutically effective amount of a composition of claim 17.

20. A method for preventing cardiac hypertrophy comprising administering to a mammalian specie in need thereof a therapeutically effective amount of a composition of claim 17.

* * * * *